United States Patent
Wang et al.

(10) Patent No.: US 6,605,679 B1
(45) Date of Patent: Aug. 12, 2003

(54) POLYMERIZATION OF OLEFINS

(75) Inventors: Lin Wang, Hockessin, DE (US); Samuel David Arthur, Wilmington, DE (US); Elizabeth Forrester McCord, Hockessin, DE (US); Yueli Wang, Morrisville, NC (US); Peter Arnold Morken, Wilmington, DE (US); Lynda Kaye Johnson, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/496,114

(22) Filed: Feb. 1, 2000

Related U.S. Application Data

(60) Division of application No. 09/120,008, filed on Jul. 21, 1998, now abandoned, which is a continuation-in-part of application No. 08/899,017, filed on Jul. 23, 1997, now abandoned.

(51) Int. Cl.[7] .................. C08F 214/18; C08F 216/02; C08F 228/02

(52) U.S. Cl. .................. 526/288; 526/243; 526/248; 526/310; 526/312

(58) Field of Search ................. 526/288, 243, 526/248, 310, 312

(56) References Cited

U.S. PATENT DOCUMENTS

| | | | | | |
|---|---|---|---|---|---|
| 5,346,924 | A | * | 9/1994 | Giuffrida | 521/28 |
| 5,425,865 | A | * | 6/1995 | Singleton | 204/252 |
| 5,627,292 | A | * | 5/1997 | Armand | 549/555 |
| 6,025,092 | A | * | 2/2000 | Doyle | 429/213 |
| 6,107,422 | A | * | 8/2000 | Wang | 526/243 |
| 6,437,011 | B2 | * | 8/2002 | Steck | 521/27 |

* cited by examiner

*Primary Examiner*—Fred Zitomer

(57) ABSTRACT

Olefins containing selected functional groups such as silyl, ether and alkenyl, and often containing a blocking group, may be copolymerized with unsubstituted olefins such as ethylene and propylene in the presence of certain coordination compounds of nickel or palladium. The resulting polymers are useful as molding resins, elastomers, in adhesives and for films.

6 Claims, No Drawings

POLYMERIZATION OF OLEFINS

CROSS REFERENCE TO RELATED APPLICATION

This application is a divisional of pending application Ser. No. 09/120,008, filed Jul. 21, 1998 abandoned, which is a continuation-in-part of application Ser. No. 08/899,017, filed Jul. 23, 1997, now abandoned.

FIELD OF THE INVENTION

Olefin (co)polymerization where the olefins contain certain functional groups such as silyl may be carried out using certain transition metal compounds as catalysts. Olefins containing other functional groups such as ester or alkenyl may be similarly polymerized and/or the polymerization improved if the olefin contains a "blocking group" such as a quaternary carbon atom.

TECHNICAL BACKGROUND

Polyolefins are useful in many areas as, for example, molding resins for toys and automotive parts, resins for film in packaging, elastomers and other uses. Many times it is desirable to copolymerize an olefin containing one or more functional groups, which may serve to later help crosslink the polymer, change the surface or other physical properties of the polymer, etc. Many olefins may be polymerized by using various transition metal compounds as polymerization catalysts, such as Ziegler-Natta or metallocene-type catalysts. However many times these polymerizations either won't proceed or proceed poorly in the presence of olefins containing functional groups.

Olefins may also be polymerized using catalysts containing late transition metals such as palladium or nickel, and sometimes functionalized olefins may be copolymerized. However, the range of useful functionalized olefins is limited, and often the efficiency of the polymerization is reduced in the presence of these olefins. Therefore more versatile and/or more efficient polymerizations of functionalized olefins are desired.

World Patent Applications 96/23010 and 97/02298 describe the polymerization of olefins, some of them containing functional groups, using certain transition metal containing compounds. The use of olefins containing blocking groups is not described in these applications.

SUMMARY OF THE INVENTION

This invention concerns a process for the polymerization of olefins, comprising, contacting a first olefin selected from the group consisting of cyclopentene, norbornene, and a compound of the formula $R^4CH{=}CHR^1$, a second olefin containing one or more of the functional groups selected from the group consisting of $-SiR^2_3$, $-CO_2R^3$, a nonconjugated ketone, $-SO_2R^7$, alkenyl, $-C(O)-O-C(O)R^4$, $-C_6F_5$, $-OR^8$, $-CO_2H$, $-OH$, $-CHO$, $-OP(O)(OR^5)_2$, $-BR^6_2$, $-SR^9$, $-SH$, ether, epoxy, and $-CONR^{68}R^{69}$, and a nickel or palladium coordination compound of

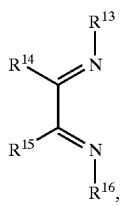
(IV)

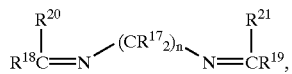
(V)

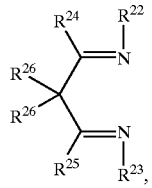
(VI)

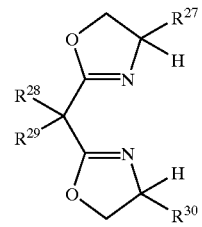
(VII)

$Ar^1Z_p$ (VIII);

$R^{31}R^{32}N-CR^{33}R^{34}(CR^{35}R^{36})_m-NR^{31}R^{32}$ (IX);

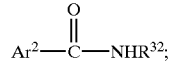
(X)

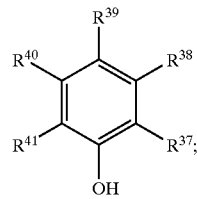
(XI)

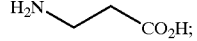
(XII)

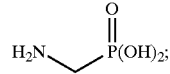
(XIII)

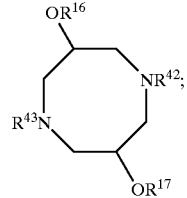
(XIV)

-continued

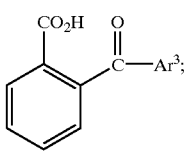   (XV)

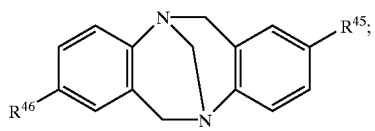   (XVI)

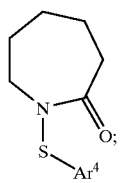   (XVII)

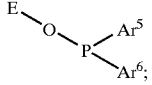   (XVIII)

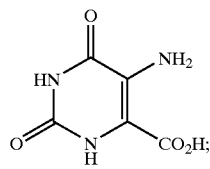   (XIX)

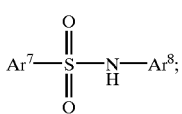   (XX)

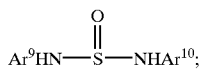   (XXI)

$R^{47}R^{48}R^{49}P$ (XXII);

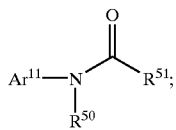   (XXIII)

and $R^{31}S—CR^{33}R^{34}(CR^{35}R^{36})_m—SR^{31}$ (XXIV);

wherein:
$Ar^1$ is an aromatic moiety with n free valencies, or diphenylmethyl;
each Z is $—NR^{52}R^{53}$ or $—CR^{54}=NR^5$;
p is 1 or 2;
E is 2-thienyl or 2-furyl;
each $R^{52}$ is independently hydrogen, benzyl, substituted benzyl, phenyl or substituted phenyl;
each $R^{54}$ is independently hydrogen or hydrocarbyl; and
each $R^{55}$ is independently a monovalent aromatic moiety;
m is 1, 2 or 3;
$R^{53}$ is hydrogen or alkyl;
each $R^{33}$, $R^{34}$, $R^{35}$, and $R^{36}$ is independently hydrogen, hydrocarbyl or substituted hydrocarbyl;

each $R^{31}$ is independently hydrocarbyl or substituted hydrocarbyl containing 2 or more carbon atoms;
each $R^{32}$ is independently hydrogen, hydrocarbyl or substituted hydrocarbyl;
$Ar^2$ is an aryl moiety;
$R^{38}$, $R^{39}$, and $R^{40}$ are each independently hydrogen, hydrocarbyl, substituted hydrocarbyl or an inert functional group;
$R^{37}$ and $R^{41}$ are each independently hydrocarbyl, substituted hydrocarbyl or an inert functional group whose $E_s$ is about —0.4 or less;
each $R^{42}$ and $R^{43}$ is independently hydrogen or acyl containing 1 to 20 carbon atoms;
$Ar^3$ is an aryl moiety;
$R^{45}$ and $R^{46}$ are each independently hydrogen or hydrocarbyl;
$Ar^4$ is an aryl moiety;
$Ar^5$ and $Ar^6$ are each independently hydrocarbyl;
$Ar^7$ and $Ar^8$ are each independently an aryl moiety;
$Ar^9$ and $Ar^{10}$ are each independently an aryl moiety or $—CO_2R^{56}$, wherein $R^{56}$ is alkyl containing 1 to 20 carbon atoms;
$Ar^{11}$ is an aryl moiety;
$R^{50}$ is hydrogen or hydrocarbyl;
$R^{51}$ is hydrocarbyl or $—C(O)—NR^{50}-Ar^{11}$;
$R^{44}$ is aryl;
$R^{47}$ and $R^{48}$ are each independently phenyl groups substituted by one or more alkoxy groups, each alkoxy group containing 1 to 20 carbon atoms;
$R^{49}$ is alkyl containing 1 to 20 carbon atoms, or an aryl moiety;
$R^{13}$ and $R^{16}$ are each independently hydrocarbyl or substituted hydrocarbyl, provided that the carbon atom bound to the imino nitrogen atom has at least two carbon atoms bound to it;
$R^{14}$ and $R^{15}$ are each independently hydrogen, hydrocarbyl, substituted hydrocarbyl, or $R^{14}$ and $R^{15}$ taken together are hydrocarbylene substituted hydrocarbylene to form a carbocyclic ring;
$R^{18}$ is hydrocarbyl or substituted hydrocarbyl, and $R^{20}$ is hydrogen, hydrocarbyl or substituted hydrocarbyl or $R^{18}$ and $R^{20}$ taken together form a ring;
$R^{19}$ is hydrocarbyl or substituted hydrocarbyl, and $R^{21}$ is hydrogen, substituted hydrocarbyl or hydrocarbyl, or $R^{19}$ and $R^{21}$ taken together form a ring;
each $R^{17}$ is independently hydrogen, substituted hydrocarbyl or hydrocarbyl, or two of $R^{17}$ taken together form a ring;
$R^{27}$ and $R^{30}$ are independently hydrocarbyl or substituted hydrocarbyl;
$R^{28}$ and $R^{29}$ are each in independently hydrogen, hydrocarbyl or substituted hydrocarbyl; and
n is 2 or 3; which is an olefin polymerization catalyst, and wherein:
each $R^1$ is independently hydrogen or alkyl;
each $R^2$ is independently hydrocarbyl, substituted hydrocarbyl, halogen, acyloxy, amino, siloxy, or $—OR^{12}$;
$R^3$ is hydrogen, hydrocarbyl or substituted hydrocarbyl;
$R^4$ is hydrocarbyl or substituted hydrocarbyl;
each $R^5$ is independently hydrocarbyl or substituted hydrocarbyl;
$R^6$ is hydrocarbyl or substituted hydrocarbyl;
$R^7$ is hydrocarbyl or substituted hydrocarbyl;
$R^8$ is hydrocarbyl or substituted hydrocarbyl;
$R^9$ is hydrocarbyl or substituted hydrocarbyl; and $R^{68}$ and $R^{69}$ are each independently hydrogen, hydrocarbyl or substituted hydrocarbyl;

and provided that:

when said functional group is alkenyl, —$OR^8$, —OH, —CHO, —OP(O)($OR^5$)$_2$, —$SR^9$, —SH, ether, epoxy, or —$CONR^{68}R^{69}$ there is a blocking group between a carbon-carbon double bond of said olefin containing one or more of the functional groups and said functional groups; and when said functional group is a nonconjugated ketone, alkenyl, —C(O)—O—C(O)$R^4$, —CO$_2$H, —OH, —CHO, —OP(O)($OR^5$)$_2$, —$SR^9$, or —SH, epoxy, said coordination compound is preferably a palladium compound.

Also disclosed herein is a compound of the formula

$$H_2C=CH-T-NR^{71}-C(O)CFR^{72}(OCF_2CFR^{72})_aOCF_2(CFR^{72})_bSO_2F, \quad \text{(XXVI)}$$

wherein:

T is alkylene or substituted alkylene;

$R^{71}$ is hydrocarbyl or substituted hydrocarbyl;

each $R^{72}$ is independently fluorine, chlorine or perfluoroalkyl containing 1 to 10 carbon atoms;

a is 0, 1 or 2; and b is 0 or an integer of 1 to 6.

Also disclosed herein is a copolymer comprising repeat units of the formula

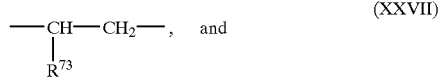

$$-CH-CH_2-, \quad \text{and} \quad \text{(XXVII)}$$
$$\phantom{-CH-}|\phantom{-CH_2-}$$
$$\phantom{-CH-}R^{73}$$

$$-CH-CH_2- \quad \text{(XXVIII)}$$
$$|$$
$$T-NR^{71}-C(O)CFR^{72}(OCF_2CFR^{72})_aOCF_2(CFR^{72})_bSO_2R^{74},$$

wherein:

T is alkylene or substituted alkylene;

$R^{71}$ is hydrocarbyl or substituted hydrocarbyl;

each $R^{72}$ is independently fluorine, chlorine or perfluoroalkyl containing 1 to 10 carbon atoms;

a is 0, 1 or 2;

b is 0 or an integer of 1 to 6;

$R^{73}$ is alkyl or hydrogen; and $R^{74}$ is hydroxyl, fluorine, chlorine, or OM, wherein M is a metal cation.

DETAILS OF THE INVENTION

In the polymerization processes and catalyst compositions described herein certain groups may be present. By hydrocarbyl is meant a univalent radical containing only carbon and hydrogen. By saturated hydrocarbyl is meant a univalent radical which contains only carbon and hydrogen, and contains no carbon-carbon double bonds, triple bonds and aromatic groups. By substituted hydrocarbyl herein is meant a hydrocarbyl group which contains one or more (types of) substituents that does not interfere with the operation of the polymerization catalyst system. Suitable substituents include halo, ester, keto (oxo), amino, imino, carboxyl, phosphite, phosphonite, phosphine, phosphinite, thioether, amide, nitrile, and ether. Preferred substituents are halo, ester, amino, imino, carboxyl, phosphite, phosphonite, phosphine, phosphinite, thioether, and amide. By (substituted) hydrocarbylene is meant a group analogous to hydrocarbyl, except the radical is divalent. By alkylene is meant a divalent radical in which the free bonds are to carbon atoms which are saturated. By substituted alkylene is meant substitution as described above for substituted hydrocarbyl. By benzyl is meant the $C_6H_5CH_2$— radical, and substituted benzyl is a radical in which one or more of the hydrogen atoms is replaced by a substituent group (which may include hydrocarbyl). By an aryl moiety is meant a univalent group whose free valence is to a carbon atom of an aromatic ring. The aryl moiety may contain one or more aromatic ring and may be substituted by inert groups. By phenyl is meant the $C_6H_5$— radical, and a phenyl moiety or substituted phenyl is a radical in which one or more of the hydrogen atoms is replaced by a substituent group (which may include hydrocarbyl). Preferred substituents for substituted benzyl and phenyl include those listed above for substituted hydrocarbyl, plus hydrocarbyl. If not otherwise stated, hydrocarbyl, substituted hydrocarbyl and all other groups containing carbon atoms, such as alkyl, preferably contain 1 to 20 carbon atoms.

Where applicable, $E_s$ refers to the steric effect of a group. The steric effect of various groupings has been quantified by a parameter called $E_s$, see R. W. Taft, Jr., J. Am. Chem. Soc., vol. 74, p. 3120–3128 (1952), and M. S. Newman, Steric Effects in Organic Chemistry, John Wiley & Sons, New York, 1956, p. 598–603. For the purposes herein, the $E_s$ values are those described in these publications. If the value for $E_s$ for any particular group is not known, it can be determined by methods described in these publications. For the purposes herein, the value of hydrogen is defined to be the same as for methyl. It is preferred that the total $E_s$ value for the ortho (or other substituents closely adjacent to the —OH group) substitutents in the ring be about –1.5 or less, more preferably about –3.0 or less. Thus in a compound such as 2,4,6-tri-t-butylphenol only the $E_s$ values for the 2 and 6 substituted t-butyl groups would be applicable.

Noncoordinating ions are mentioned and useful herein. Such anions are well known to the artisan, see for instance W. Beck., et al., Chem. Rev., vol. 88, p. 1405–1421 (1988), and S. H. Strauss, Chem. Rev., vol. 93, p. 927–942 (1993), both of which are hereby included by reference. Relative coordinating abilities of such noncoordinating anions are described in these references, Beck at p. 1411, and Strauss at p. 932, Table III. Useful noncoordinating anions include $SbF_6^-$, $BAF$, $PF_6^-$, or $BF_4^-$, wherein BAF is tetrakis[3,5-bis(trifluoromethyl)phenyl]borate.

A neutral Lewis acid or a cationic Lewis or Bronsted acid whose counterion is a weakly coordinating anion is also present as part of the catalyst system. By a "neutral Lewis acid" is meant a compound which is a Lewis acid capable of abstracting $Q^-$ or $S^-$ from (XXV) to form a weakly coordinating anion. The neutral Lewis acid is originally uncharged (i.e., not ionic). Suitable neutral Lewis acids include $SbF_5$, $Ar_3B$ (wherein Ar is aryl), and $BF_3$. By a cationic Lewis acid is meant a cation with a positive charge such as $Ag^+$, $H^+$, and $Na^+$.

In those instances in which (XXV) (and similar catalysts which require the presence of a neutral Lewis acid or a cationic Lewis or Bronsted acid), does not contain an alkyl or hydride group already bonded to the metal (i.e., neither Q or S is alkyl or hydride), the neutral Lewis acid or a cationic Lewis or Bronsted acid also alkylates or adds a hydride to the metal, i.e., causes an alkyl group or hydride to become bonded to the metal atom, or a separate (from W) compound is added to add the alkyl or hydride group.

A preferred neutral Lewis acid, which can alkylate the metal, is a selected alkyl aluminum compound, such as $R^9_3Al$, $R^9_2AlCl$, $R^9AlCl_2$, and "$R^9AlO$" (alkylaluminoxanes), wherein $R^9$ is alkyl containing 1 to 25 carbon atoms, preferably 1 to 4 carbon atoms. Suitable alkyl aluminum compounds include methylaluminoxane (which is an oligomer with the general formula $[MeAlO]_n$), $(C_2H_5)_2AlCl$, $C_2H_5AlCl_2$, and $[(CH_3)_2CHCH_2]_3Al$. Metal hydrides such as $NaBH_4$ may be used to bond hydride groups to the metal M.

In the polymerization process herein the first olefin, which may be of the formula $R^1CH=CHR^1$ is copolymerized with a second olefin. In preferred first olefins, both of $R^1$ are hydrogen (the olefin is ethylene), or one of $R^1$ is hydrogen and the other is n-alkyl containing 1 to 20 carbon atoms. In the latter compound it is preferred that the n-alkyl group contains 1 carbon atom (the olefin is propylene). More than one first olefin and/or second olefin may be used, but at least one of each must be used.

The second olefin is a functional olefin that contains another group besides the carbon-carbon alkenyl double bond (the other functional group may also be a carbon-carbon alkenyl double bond). These two groups in the second olefin may (in some cases must) be separated by a blocking group. By a blocking group is meant a group that will not allow the carbon-carbon double bond and/or the functional group to isomerize so that these two groups may be directly conjugated to each other. By directly is meant there are no intervening groups between the two subject groups. The blocking group should not be able to readily form a π-benzyl group or a polymerizable vinyl ether group with the carbon-carbon double bond under the polymerization conditions, so p-phenylene or a simple aliphatic ether group such as —$CH_2CH_2O$— are not blocking groups. However, tetrafluoro-p-phenylene and an ether such as —$CH_2CH_2OCF_2CF_2$— are blocking groups since they are so electron poor that they normally don't readily form n-benzyl group or a polymerizable vinyl ether group, respectively. Useful blocking groups include a quaternary carbon atom (a carbon atom bound to 4 other atoms, none of which is a hydrogen atom, in other words the quaternary carbon atom does not have any multiple bonds to any other element), an ester group, an amide group, a sulfone group, tetrafluoro-p-phenylene, a silyl group, a borane group, a carbonate group, and ammonium cation. Preferred blocking groups are a quaternary carbon atom, especially a quaternary carbon atom bound to 4 other carbon atoms, an ester group, a sulfone group, and —$(CF_2)_n$— wherein n is an integer of 2 to 20. Note that some blocking groups may also be the "functional" groups of the second olefin. Whether a blocking group is required in a certain second olefin or not, it has been found that the yield of polymer when a blocking group is present is often greatly improved over using a functional olefin which does not contain a blocking group (if any polymer is obtained at all in the latter case). It is therefore preferred in all second olefins herein to have a blocking group present.

The polymers made herein are copolymers of the first and second olefins, although homopolymers of the second olefin may also be made if the first olefin is not present in the polymerization. Many of the copolymers made herein are unique since olefin copolymers with containing these functional groups have not been made. Such copolymers may include those with the functional groups such as —$SiR^2_3$, a nonconjugated ketone, —$SO_2R^7$, alkenyl, —C(O)—O—C(O)$R^4$, —$C_6F_5$, —$OR^8$, —OH, —CHO, —OP(O)($OR^5$)$_2$, —$BR^6_2$, —$SR^9$, —SH, ether, epoxy, and —$CONR^{68}R^{69}$, particularly if a blocking group is also present in the second olefin. In addition these polymers may have branching patterns that are "abnormal" in the sense that branches may be present that do not correspond to the branch expected if the olefin is simply incorporated into the polymer through the existing olefinic bond. For a discussion of such branching, see World Patent Applications 96/23010 and 97/02298. In addition to the abnormal number of carbon atoms in such branches and/or the abnormal number of branches, in some instances the functional-groups of the second monomer may be present at the end of branches of the "wrong" length. Such polymers may also be novel.

Preferred functional groups in the second olefin are —$SiR^2_3$ wherein all of $R^2$ are chlorine or —$OR^{70}$ wherein $R^{70}$ is n-alkyl containing 1 to 6 carbon atoms, epoxide or alkenyl.

In olefins in which the —$SiR^2_3$ group is present a preferred formula is $H_2C=CH(CH_2)_qSiR^2_3$ wherein q is 0 or an integer of 1 to 20, more preferably an integer of 1 to 8. It is preferred that at least one of $R^2$ is chloro or —$OR^{57}$, wherein $R^{57}$ is alkyl containing 1 to 20 carbon atoms, more preferably methyl or ethyl, and the remainder of $R^2$ are alkyl containing 1 to 6 carbon atoms or phenyl, more preferably methyl. In one preferred form, all of $R^2$ are chloro or —$OR^{57}$.

Preferred olefins in which —$CO_2R^3$ are present have the formula

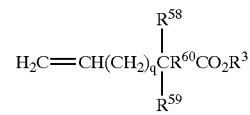

wherein q is 0 or an integer of 1 to 20, $R^{58}$ and $R^{59}$ are hydrocarbyl or substituted hydrocarbyl, preferably alkyl containing 1 to 20 carbon atoms, and $R^{60}$ is a covalent bond or alkylene containing 1 to 20 carbon atoms. In more preferred olefins of this type, q is 1 and/or $R^{58}$ and/or $R^{59}$ are methyl, and $R^{60}$ is a covalent bond or —$(CH_2)_s$— wherein s is an integer of 1 to 6, and/or $R^3$ is alkyl or hydrogen.

Preferred olefins which have an amide group present have the formula

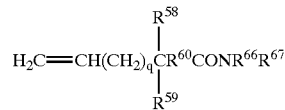

wherein $R^{58}$, $R^{59}$, $R^{60}$, $R^{66}$, $R^{67}$ and q are as defined above. In all amides it is preferred that $R^{66}$ and $R^{67}$ are hydrocarbyl or substituted hydrocarbyl. Preferred groups for $R^{58}$, $R^{59}$, $R^{60}$ and q are as described above.

When the functional group in the second olefin is alkenyl, it is preferred that it has the formula

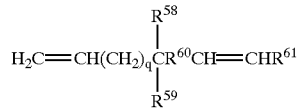

wherein q is 0 or an integer of 1 to 20, $R^{58}$ and $R^{59}$ are hydrocarbyl or substituted hydrocarbyl, preferably alkyl containing 1 to 20 carbon atoms, $R^{60}$ is a covalent bond or alkylene containing 1 to 20 carbon atoms, and $R^{61}$ is hydrogen or alkyl containing 1 to 20 carbon atoms. In more preferred olefins of this type, q is 1 and/or $R^{58}$ and/or $R^{59}$ are methyl, and/or $R^{60}$ is a covalent bond or —$(CH_2)_s$— wherein s is an integer of 1 to 6, and/or $R^{61}$ is hydrogen or methyl.

When the second olefin contains ether a preferred formula for the ether bearing moiety is

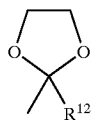
(III)

wherein $R^{12}$ is alkyl containing 1 to 20 carbon atoms, more preferably is methyl, or

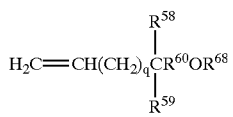

wherein $R^{58}$, $R^{59}$, $R^{60}$, $R^{66}$, $R^{67}$ and q are as defined above, and $R^{68}$ is hydrocarbyl or substituted hydrocarbyl, more preferably alkyl containing 1 to 20 carbon atoms. Preferred groups for $R^{58}$, $R^{59}$, $R^{60}$ and q are as described above.

When the functional group is an epoxide, a preferred compound is

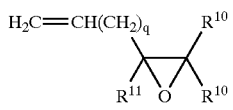

wherein each of $R^{10}$ is hydrogen, hydrocarbyl or substituted hydrocarbyl, $R^{11}$ is hydrocarbyl or substituted hydrocarbyl, and q is 0 or an integer of 1 to 20, or a compound of the formula

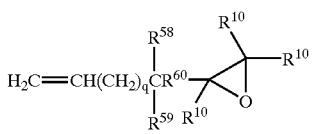

wherein q, $R^{58}$, $R^{59}$, $R^{60}$ and $R^{10}$ are as defined above. In preferred epoxides q, $R^{58}$, $R^{59}$, $R^{60}$ are as defined above for preferred compounds, and/or $R^{11}$ is preferably alkyl, more preferably methyl, and/or $R^{11}$ is alkyl, more preferably methyl. Note that a quaternary carbon atom in the epoxide ring itself may act as a blocking group.

When the functional group in the second olefin is a nonconjugated ketone, a preferred olefin is $H_2C$=$CHR^{64}C(O)R^{65}$, wherein $R^{64}$ is alkylene containing 1 to 20 carbon atoms and $R^{65}$ is alkyl containing 1 to 20 carbon atoms. In more preferred olefins $R^{64}$ is —$(CH_2)_s$— wherein s is an integer of 1 to 6, and/or $R^{65}$ is methyl.

Of the compounds (or their complexes) (IV) through (XXIV) used in the polymerization processes, (IV) is preferred. In all cases herein where (IV) appears, including as a ligand, it is preferred that $R^{13}$ and $R^{16}$ are each independently hydrocarbyl provided that the carbon atom bound to the imino nitrogen atom has at least two carbon atoms bound to it; and $R^{14}$ and $R^{15}$ are each independently hydrogen, hydrocarbyl, or $R^{14}$ and $R^{15}$ taken together are hydrocarbylene to form a ring. Some useful combinations and/or individual groupings for $R^{13}$, $R^{14}$, $R^{15}$ and $R^{16}$ are shown in Table I.

TABLE 1*

| $R^{13}$ | $R^{14}$ | $R^{15}$ | $R^{16}$ |
|---|---|---|---|
| 2,6-i-PrPh | Me | Me | 2,6-i-PrPh |
| 2,6-i-PrPh | H | H | 2,6-i-PrPh |
| 2,6-MePh | H | H | 2,6-MePh |
| 2,6-MePh | Me | Me | 2,6-MePh |
| 2,6-i-PrPh | Me | Me | 2,6-i-PrPh |
| 2,6-i-PrPh | Me | Me | 2,6-i-PrPh |
| 2,6-i-PrPh | Me | Me | 2,6-i-PrPh |
| 2,6-i-PrPh | H | H | 2,6-i-PrPh |
| 2,4,6-MePh | Me | Me | 2,4,6-MePh |
| 2,6-i-PrPh | An | An | 2,6-i-PrPh |
| 2,6-i-PrPh | Me | Me | 2,6-i-PrPh |
| Ph | Me | Me | Ph |
| 2,6-EtPh | Me | Me | 2,6-EtPh |
| 2,6-EtPh | Me | Me | 2,6-EtPh |
| 2-t-BuPh | Me | Me | 2-t-BuPh |
| 1-Np | Me | Me | 1-Np |
| $Ph_2CH$ | H | H | $Ph_2CH$ |
| 2-PhPh | Me | Me | 2-PhPh |
| Ph | a | a | Ph |
| Ph | Me | Me | Ph |
| Ph | Ph | Ph | Ph |
| $Ph_2CH$ | H | H | $Ph_2CH$ |
| $Ph_2CH$ | H | H | $Ph_2CH$ |
| 2,4,6-MePh | An | An | 2,4,6-MePh |
| 2,4,6-MePh | Ph | Ph | 2,4,6-MePh | a —$CMe_2CH_2CMe_2$—.
*In Table 1 and otherwise herein the following abbreviations are used: Me = methyl; Et = ethyl; Br = bromo; i-Pr = isopropyl; Ph = phenyl; and An = 1,8-naphthylene,

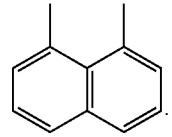

To indicate substitution on a phenyl ring, the nomenclature is abbreviated, the number of ring positions indicating how many of the substituents are on the ring. For instance, 4-Br-2,6-MePh indicates 4-bromo-2,6-dimethylphenyl.

For (IV) through (XXIV) preferred formulas and compounds (as ligands for polymerization catalysts) are found in World Patent Applications 96/23010 and 97/02298, both of which are hereby included by reference, and preferred grouping and compounds in these applications are also preferred herein. However the compound numbers and group (i.e., $R^x$) numbers in these Applications may vary from those herein, but they are readily convertible.

There are many different ways of preparing active polymerization catalysts of Ni or Pd coordination compounds of compounds (IV) through (XXIV), many of which are described in World Patent Applications 96/23010 and 97/02298, and those so described are applicable herein. "Pure" compounds which themselves may be active polymerization catalysts may be used, or the active polymerization catalyst may be prepared in situ by a variety of methods.

For instance, olefins may be polymerized by contacting, at a temperature of about −100° C. to about +200° C. a first compound W, which is a neutral Lewis acid capable of abstracting either $Q^-$ or $S^-$ to form $WQ^-$ or $WS^-$, provided that the anion formed is a weakly coordinating anion; or a cationic Lewis or Bronsted acid whose counterion is a weakly coordinating anion; a second compound of the formula

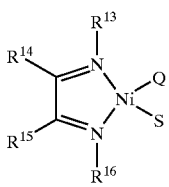
(XXV)

and one or more olefins wherein:

M is Ni or Pd;

$R^{13}$ and $R^{16}$ are each independently hydrocarbyl or substituted hydrocarbyl, provided that the carbon atom bound to the imino nitrogen atom has at least two carbon atoms bound to it;

$R^{14}$ and $R^{15}$ are each independently hydrogen, hydrocarbyl, substituted hydrocarbyl, or $R^{14}$ and $R^{15}$ taken together are hydrocarbylene or substituted hydrocarbylene to form a ring;

Q is alkyl, hydride, alkoxide, chloride, iodide, or bromide; and

S is alkyl, hydride, alkoxide, chloride, iodide, or bromide.

In this instance it is preferred that W is an alkyl aluminum compound. Other methods for preparing active polymerization catalyst will be found in these patent application and in the Examples herein.

Which polymerization catalysts or types of catalysts will polymerize the first olefin types herein will also be found in World Patent Applications 96/23010 and 97/02298. It is believed that any catalyst that will polymerize α-olefins of the formula $H_2C=CHR^{66}$ wherein $R^{66}$ is n-alkyl will also copolymerize any of the second olefins herein. First monomers useful herein include ethylene, propylene, other α-olefins of the formula $R^{67}CH=CH_2$, wherein $R^{67}$ is n-alkyl containing 2 to about 20 carbon atoms, cyclopentene, norbornene, and 2-butene. Preferred monomers are ethylene, propylene and cyclopentene.

Likewise, conditions for such polymerizations will also be found in these patent applications. Briefly, the temperature at which the polymerization is carried out is about −100° C. to about +200° C., preferably about −20° C. to about +80° C. The polymerization pressure which is used with a gaseous olefin is not critical, atmospheric pressure to about 275 MPa, or more, being a suitable range. With a liquid monomer the monomer may be used neat or diluted with another liquid (solvent) for the monomer. The ratio of W:(XXV), when W is present, is preferably about 1 or more, more preferably about 10 or more when only W (no other Lewis acid catalyst) is present. These polymerizations may be batch, semi-batch or continuous processes, and may be carried out in liquid medium or the gas phase (assuming the monomers have the requisite volatility). These details will also be found in World Patent Applications 96/23010 and 97/02298.

In (XXVI) and (XXVIII), where applicable, it is preferred that T is —(CH$_2$)$_n$— wherein n is an integer of 1 to 10, more preferably n is 1, and/or $R^{71}$ is alkyl, more preferably methyl, and/or each $R^{72}$ is fluorine or trifluoromethyl, more preferably fluorine, and/or a is 0, and/or b is 1, and/or $R^{74}$ is fluorine, hydroxyl or OM, wherein M is an alkali metal cation. In (XXVII) it is preferred that $R^{73}$ is hydrogen or n-alkyl, more preferably hydrogen or methyl and especially preferably hydrogen.

(XXVI) may be made generally as described herein in Example 40 by the reaction of the appropriate alkenyl secondary amine with and acyl halide of the appropriate fluorinated sulfonyl fluoride. Such fluorinated sulfonyl fluorides can be made by methods known in the art, see for instance Siegemund, et al., in Ullmann's Encyclopedia of Industrial Chemistry, 5$^{th}$ Ed., Vol. All, VCH Verlagsgesellschaft mbH, Weinheim (1988), p. 374 and M. Yamabe, et al., in Organofluorine Chemistry: Principles and Commercial Application, R. E. Banks, et al., Ed., Plenum Press, New York (1994), p. 403–411.

Formation of polymers made from repeat units comprising (XXVII) and (XXVIII) can be made by methods described herein, see for instance Example 41. Once the polymer in which (XXVIII) is present and in which $R^{74}$ is fluorine is made, the other derivatives with different groups for $R^{74}$ can be made. For example, the fluorine may be converted to chlorine by reaction with a silicon chloride. The sulfonyl fluoride may be hydrolyzed by reaction with water to the sulfonic acid. If a base is present during the hydrolysis, such as an alkali metal hydroxide, the metal salt will be formed. It will be realized by the artisan that for other than monovalent metal cations, an appropriate ratio of metal to sulfonate groups must be present to balance the ionic charges, and the group "OM" is meant to include such balancing. The sulfonic acid and sulfonate salts may be readily interconverted by reaction with a strong acid or strong base, as appropriate.

The polymers made herein are useful as molding resins, elastomers, in adhesives and for films. Because of the presence of functional groups they may be readily crosslinkable, have useful surface properties, or be especially compatible with other polymers.

In the Examples, the following abbreviations are used:

DSC—Differential Scanning Calorimetry
FTIR—Fourier transform infrared spectroscopy
GPC—Gel Permeation Chromatography
MAO—methylaluminoxane
MMAO—modified (contains sec-butyl groups.) MAO
Mn—number average molecular-weight
Mw—weight average molecular weight
PE—polyethylene
PMAO—see MAO
RT—room temperature
TCB—1,2,4-triclhorobenzene
TCE—1,1,2,2-tetrachloroethane
Tg—glass transition temperature (measured by DSC at 10° C./min, the midpoint of the transition taken as the Tg)
THF—tetrahydrofuran In the Examples transition metal complexes of (IV) are indicated by the use of the abbreviation "DAB". Immediately before the DAB are the groups represented by $R^{13}$ and $R^{16}$ while immediately after DAB are the groups represented by $R^{14}$ and $R^{15}$. The other groups coordinated to the metal and/or free anions present in the compound are also indicated.

EXAMPLE 1

Ethylene Copolymer of Silane-containing Acrylate

The compound PdCH$_2$CH$_2$CH$_2$C(O)OCH$_3$[(2,6-i-Pr Ph)$_2$DABMe$_2$]SbF$_6$ (0.0848 g, 0.1 mmol) and CH$_2$=CHCO$_2$(CH$_2$)$_2$SiCl$_3$ (2.5 g, 0.010 mol) were dissolved in 40 mL CH$_2$Cl$_2$. The solution was placed under 1 atm of ethylene and was stirred for 15 h at RT. Solvent was then evaporated.

The residue was dissolved in 40 mL of $CH_2Cl_2$ and filtered through Celite® in a dry box. After evaporation of solvent, the residue was redissolved in 10 mL of $CH_2Cl_2$. Methanol (ca. 4 mL) was added dropwise to the solution, followed by addition of 70 mL of methanol to precipitate the product. The oil was isolated and was redissolved in 10 mL of $CH_2Cl_2$. Methanol(70 mL) was used to reprecipitate the product. The product was isolated and vacuum dried. One g of a viscous oil was obtained. Based on $^1H$ NMR, the silane incorporation (in terms of $—Si(OCH_3)_3$) was 0.6 mole %. The polymer was highly branched based on $^1H$ NMR (116Me/1000$CH_2$, 116 methyl groups per 1000 methylene carbon atoms in the polymer). The copolymer exhibits a Tg of $-67°$ C. by DSC. GPC (THF, polystyrene standard): Mw=21,600; Mn=13,700; Mw/Mn=1.6.

EXAMPLE 2

Ethylene Copolymer of 7-Octenyltrichlorosilane

The compound $PdCH_2CH_2CH_2C(O)OCH_3[(2,6$-i-PrPh$)_2DABMe_2]SbF_6$ (0.0848 g, 0.1 mmol) and $CH_2$=$CH_2(CH_2)_6SiCl_3$ (2.5 g, 0.010 mol) were dissolved in 40 mL $CH_2Cl_2$. The solution was placed under 1 atm of ethylene under stirring for 48.5 h at RT. Solvent was then evaporated. In a dry box, the residue was dissolved in 20 mL heptane and then 20 mL $HC(OMe)_3$ was added. The mixture was refluxed for 1 h. Methanol (ca. 60 mL) was added to the room temperature solution. The upper layer was decanted. The residue was dissolved in 20 mL of pentane, followed by addition of 60 mL methanol. The oil was isolated and vacuum dried. Three g of a viscous oil was obtained. Based on $^1H$ NMR, the silane incorporation (in terms of $—Si(OCH_3)_3$) was 4.35 mole %. The polymer was highly branched based on $^1H$ NMR (80Me/1000$CH_2$). The copolymer exhibited a Tg of $-69°$ C. by DSC. GPC (THF, polystyrene standard): Mw=329,000; Mn=108,000; Mw/Mn=3.0.

EXAMPLE 3

The compound $PdCH_2CH_2CH_2C(O)OCH_3[(2,6$-i-PrPh$)_2DABMe_2]SbF_6$ (0.0848 g, 0.1 mmol) and $CH_2$=$CH_2(CH_2)_6SiCl_3$ (2.5 g, 0.010 mol) were dissolved in 40 mL $CH_2Cl_2$. The solution was placed under 1 atm of ethylene under stirring for 60 h at RT. Solvent was then evaporated. In a dry box, the residue was dissolved in 10 mL of methylene chloride and then 60 mL of slightly wet acetone was added. The upper layer was decanted. To the residue was added 15 mL of methylene chloride. Some polymer couldn't be redissolved at this point. Another 60 mL of acetone was added. The product was isolated and vacuum dried. An elastic white solid was obtained.

This Example demonstrated that the above —$SiCl_3$ containing ethylene copolymer can be easily crosslinked by trace amounts of water.

EXAMPLE 4

Synthesis of Silane-Containing Ethylene Copolymer

A 5.1-mg (0.0082-mmol) sample of $[(2,6$-i-PrPh$)_2DABMe_2]NiBr_2$ was placed in a Parr® 600-mL stirred autoclave and 200 mL of dry hexane (dried and stored over molecular sieves and kept under nitrogen) was added. The solvent was saturated with ethylene and was heated to 60° C., and a solution of 1.0 g (4.1 mmol) of 7-octenyltrichlorosilane in 5 mL dry toluene was injected into the autoclave through a head port. Then 1.0 mL of modified methylalumoxane (Akzo MMAO-3A; nominal 1.97M in toluene; contains about 30% isobutyl groups) was injected into the autoclave. The autoclave was pressured to 690 kPa with ethylene and was stirred for 30 min at 60° C. The ethylene was vented and 9 mL anhydrous n-propanol (distilled from metallic sodium) was injected into the autoclave to stop polymerization and to convert the trichlorosilane groups to tri-n-propoxysilane groups in situ. The autoclave contained a solution of polyethylene with no insoluble polymer. The polymer was precipitated from dried n-propanol under nitrogen and dried first under a nitrogen stream at RT and then under high vacuum to yield 7.7 g (67,000 catalyst turnovers/hr) of rubbery polyethylene which was soluble in chloroform. Proton NMR revealed 0.2–0.3 mol % silane incorporation, which is ~3 wt % silane incorporation as the tri-n-propyl ester. Proton NMR also showed a branching level of 115 methyl groups per 1000 methylene chain units. GPC (TCB; 135° C.; PE standard): Mn=173,000; Mw=441,000; Mw/Mn=2.55.

EXAMPLE 5

Synthesis of Silane-Containing Ethylene Copolymer

A 5.6 mg (0.0090 mmol) sample of $[(2,6$-i-PrPh$)_2DABMe_2]NiBr_2$ was placed in a Parr® 600 mL stirred autoclave and 200 mL of dry hexane was added. The solvent was saturated with ethylene and was heated to 60° C., and a solution of 3.0 g (12.2 mmol) of 7-octenyltrichlorosilane in 5 mL dry toluene was injected into the autoclave through a head port. Then 1.0 mL of modified methylalumoxane (Akzo MMAO-3A; nominal 1.97M in toluene; contains about 30% isobutyl groups) was injected into the autoclave. The autoclave was pressured to 690 kPa with ethylene and was stirred for 30 min at 60° C. The ethylene was vented and 9 mL anhydrous n-propanol (distilled from metallic sodium) was injected into the autoclave to stop polymerization. The reaction mixture was stirred for 10 min to convert the trichlorosilane groups to tri-n-propoxysilane groups. The autoclave contained hexane-soluble polyethylene with no insoluble polymer. The polymer was precipitated from dried n-propanol under nitrogen and dried first under a nitrogen stream at RT and then under high vacuum to yield 10.4 g (83,000 catalyst turnovers/hr) of rubbery polyethylene which was soluble in chloroform or chlorobenzene. Proton NMR revealed 0.5 mol % silane incorporation, which is 5.6 wt % silane incorporation as the tri-n-propyl ester. Proton NMR also showed a branching level of 121 methyl groups per 1000 methylene groups. GPC (TCB; 135° C.; PE standard): Mn=181,000; Mw=354,000; Mw/Mn=1.96.

EXAMPLE 6

Crosslinking Soluble Silane-Containing Polymer

A small sample (~0.1 g) of the soluble polymer of Example 5 was dissolved in 10 mL hot chlorobenzene. in a screw cap vial. One mL of water containing 3 drops of trifluoroacetic acid was added and the mixture was heated at 60° C. and stirred in the capped vial for 18 h. After about 3 or 4 h, the initially clear, two-phase solution became a swollen, flabby gel of crosslinked polyethylene which had imbibed all the chlorobenzene.

EXAMPLE 7

Crosslinking Soluble Silane-Containing Polymer

A 0.4 g sample of the soluble polymer of Example 5 was stirred with 15 mL of chloroform at RT under nitrogen for about a week. There were some small gel particles present, but the polymer appeared to be mostly soluble. About 8 mL of the clear polymer solution was poured into a 70 mm diameter crystallizing dish and the solvent was evaporated at RT, first at 1 atm and then under high vacuum for 3 days. The dish was then filled with 50 mL of 2% aqueous trifluoroacetic acid and the dish was covered and allowed to stand on a hot plate at 60° C. overnight. The crosslinked polymer film became translucent and was very difficult to pull off the glass surface. On stretching, a piece of the crosslinked polymer film broke cleanly at a few hundred percent elongation. It was insoluble and did not swell very much in boiling chlorobenzene.

Another film was cast in a second dish with the remaining solution of the soluble polymer of Example 5 and this film was also held under high vacuum to remove solvent. This polymer film was peeled off the glass without further treatment. The untreated film was clear and drew easily on stretching to many hundred percent elongation before breaking. The first film of this Example was clearly stronger and "snappier" than the second untreated, uncrosslinked film.

EXAMPLE 8

Synthesis of 3,3-Dimethyl-5-hexene-1,2-epoxide

In a dry box, 2.4 g NaH (0.1 mol) was suspended in 75 mL anhydrous THF. To this stirring mixture was added 12.8 g (0.1 mol) trimethylsulfoxonium chloride. The mixture was brought to gentle reflux for 2 h. Temperature was then lowered to 55° C. and 10 g 2,2-dimethyl-4-pentenal in 50 mL THF was added slowly. The addition lasted ca. 1.5 h. When addition was complete, the solution was stirred at 55° C. for another h, then overnight at RT. The volume of the solvent was reduced by half. The flask was then taken out of the dry box. Water and pentane were added to extract product. The pentane layer was washed twice with water and dried with anhydrous $Na_2SO_4$. Evaporation of pentane gave a liquid that was nearly colorless. The product was allowed to pass through a short silica column by eluting with hexane/ethyl acetate(30:1). Pure product was obtained upon evaporation of the solvents. Yield 67%. $^1H$ NMR($CDCl_3$): $\delta 0.96$(s, 3H, $—CH_3$); 0.99(s, 3H, $—CH_3$); 2.18(m, 2H, $CH_2=CH—CH_2—$); 2.73(m, 2H, $—CH_2—O—$); 2.88(m, 1H, $—CH—O—$); 5.15(m, 2H, $CH_2=CH—$); 5.95(m, 1H, $CH_2=CH—$)

EXAMPLE 9

Synthesis of the Ethylene Copolymer of 3,3-Dimethyl-5-hexene-1,2-epoxide $PdCH_2CH_2CH_2C(O)OCH_3[(2,6\text{-i-PrPh})_2DABMe_2]SbF_6$ (0.0848 g, 0.1 mmol) and 3,3-dimethyl-5-hexene-1,2-epoxide (2.86 g, 0.023 mole) were dissolved in 40 mL $CH_2Cl_2$. The solution was placed under 1 atm of ethylene under stirring for 48 h at RT. Solvent was evaporated. The oil was dried under full vacuum overnight. Product (8.05 g) was obtained. Based on $^1H$ NMR ($CD_2Cl_2$), the epoxide incorporation was 5.7 mole % {$\delta 2.52$(m, 2H, $—CH_2—O—$); 2.66(t, 1H, $—CH—O—$), the $—CMe_2—$ resonances overlapped with that of the methyls (0.8–1.0) on the copolymers, the methylene peaks overlapped with that of the copolymers (1.1–1.4). The polymer was highly branched based on $^1HNMR$(86Me/1000$CH_2$). GPC (THF, polystyrene standard): Mw=146,000; Mn=72,700; Mw/Mn=2.0.

EXAMPLE 10

Synthesis of the Ethylene Copolymer of 3,3-Dimethyl-5-hexene-1,2-epoxide $PdCH_2CH_2CH_2C(O)OCH_3[(2,6\text{-i-PrPh})_2DABMe_2]SbF_6$ (0.0848 g, 0.1 mmol) and 3,3-dimethyl-5-hexene-1,2-epoxide (1.0 g, 0.0079 mol) were dissolved in 40 mL $CH_2Cl_2$. The solution was placed under 1 atm of ethylene under stirring for 27 h at RT. The reaction mixture was slightly warm. Solvent was evaporated. The oil was dried under full vacuum overnight. 20.1 g product was obtained. Based on $^1H$ NMR($CD_2Cl_2$), the epoxide incorporation was 1.1 mole % {$\delta 2.52$(m, 2H, $—CH_2—O—$); 2.66(t, 1H, $—CH—O—$), the $—CMe_2—$ resonances overlapped with that of the methyls (0.8–1.0) on the copolymers, the methylene peaks overlapped with that of the copolymers (1.1–1.4). The polymer was highly branched based on $^1H$ NMR(115Me/1000$CH_2$). It exhibited a Tg of −40° C. by DSC. GPC (THF, polystyrene standard): Mw=188,000; Mn=98,200; Mw/Mn=1.9.

EXAMPLE 11

Synthesis of 2,,2-dimethyl-4-pentenol

In a dry box, 5 g 2,2-dimethyl-4-pentenal was mixed with 40 mL anhydrous THF. $NaBH_4$ (3.376 g) was added in portions. Soon the solution became hot. More THF was added to lower the temperature. The mixture was stirred overnight at RT. The flask was taken out of the dry box. Water and $CH_2Cl_2$ were added to the mixture. The $CH_2Cl_2$ layer was separated, washed with water twice and dried with $Na_2SO_4$. Evaporation of $CH_2Cl_2$ gave 4.3 g pure product. $^1H$ NMR($CDCl_3$): $\delta 1.00$(s, 6H, $—CMe_2—$); 2.15(d, 2H, $CH_2=CH—CH_2—$); 3.44(s, 2H, $—CH_2OH$); 5.15(d, 2H, $CH_2=CH—$); 5.95(m, 1H, $CH_2=CH—$).

EXAMPLE 12

Synthesis of the Ethylene Copolymer of 2,2-Dimethyl-4-penten-1-ol $PdCH_2CH_2CH_2C(O)OCH_3[(2,6\text{-i-PrPh})_2DABMe_2]SbF_6$ (0.0848 g, 0.1 mmol) and 2,2-dimethyl-4-penten-1-ol (4.0 g, 0.035 mol) were dissolved in 40 mL $CH_2Cl_2$. The solution was placed under 1 atm of ethylene under stirring for 48 h at RT. Solvent was evaporated. The oil product contained some unreacted comonomer. This was dissolved in a small amount of methylene chloride followed by addition of methanol. The oil was isolated and was dried under full vacuum overnight. Based on $^1H$ NMR($CDCl_3$), the alcohol incorporation was 6.2 mole % {$\delta 3.43$(s, 2H, $—CH_2OH$), the $—CMe_2—$ resonances overlapped with that of the methyls (0.8–1.0) on the copolymers, the methylene peaks overlapped with that of the copolymers (1.1–1.4). The polymer was highly branched based on $^1H$ NMR(157Me/1000$CH_2$). The copolymer exhibited a Tg of −57° C. by DSC. GPC (THF, polystyrene standard): Mw=6,600; Mn=5,060; Mw/Mn=1.3.

EXAMPLE 13

Synthesis of 2,2-Dimethyl-4-pentenyl Methyl Ether

Under nitrogen, 2.211 g NaH was suspended in 50 mL dry ether in a three-necked round bottom flask. Anhydrous $(CH_3)_2SO$ (5.0 mL) was added. The flask was cooled with ice. 2,2-Dimethyl-4-penten-1-ol (7.0 g) in 13 mL anhydrous ether was added dropwise through an addition funnel. The solution was then refluxed overnight. Upon cooling in ice, 43.56 g $CH_3I$ (5 eq) was added through an addition funnel. Soon a white precipitate was seen. The slurry was refluxed for 4 h. Upon cooling, water and ether were added to the mixture. The ether layer was separated, washed with water twice and dried with $Na_2SO_4$. Careful evaporation of ether (the product has a low b.p.) gave 2.0 g pure product. $^1$H NMR(CDCl$_3$): δ0.86(s, 6H, —CMe$_2$—); 2.00.(d, 2H, CH$_2$=CH—CH$_2$—); 3.05(s, 2H, , —CH$_2$OMe); 3.33(s, 3H, —CH$_2$OMe); 5.00(m, 2H, CH$_2$=CH—); 5.80(m, $^1$H, CH$_2$=CH—)

EXAMPLE 14

Synthesis of the Ethylene Copolymer of 2,2-Dimethyl-4-pentenyl Methyl Ether

The compound PdCH$_2$CH$_2$CH$_2$C(O)OCH$_3$[(2,6-i-Pr Ph)$_2$DABMe$_2$]SbF$_6$ (0.0848 g, 0.1 mmol) and 2,2-dimethyl-4-pentenyl methyl ether (1.71 g, 0.013 mol) were dissolved in 40 mL CH$_2$Cl$_2$. The solution was placed under 1 atm of ethylene under stirring for 41 h at RT. Solvent was evaporated. The oil was dried under full vacuum overnight. Product (15.5 g) was obtained. Based on $^1$H NMR(CD$_2$Cl$_2$), the ether incorporation was 2.1 mole % {δ3.16(s, 2H, —CH$_2$—O—); 3.44(s, 3H, —OCH$_3$), the —CMe$_2$— resonances overlapped with that of the methyls (0.8–1.0) on the copolymers, the methylene peaks overlapped with that of the copolymers (1.1–1.4). The polymer was highly branched based on $^1$H NMR(127Me/1000CH$_2$). The copolymer exhibited a Tg of —61° C. by DSC. GPC (THF, polystyrene standard): Mw=125,000; Mn=69,100; Mw/Mn=1.8.

EXAMPLE 15

Synthesis of 2-Methyl-2-(3-butenyl)-1,3-dioxolane

In a 200 mL RB flask, 5-hexen-2-one (37.18 g, 0.3788 mol) was mixed with ethylene glycol (23.49 g, 0.3788 mol), 0.72 g p-toluenesulfonic acid monohydrate and 40 mL toluene. A graduated water collector and a reflux condenser were connected to the flask. The mixture was refluxed overnight. The reaction was completed as shown by the amount of water collected (ca. 7 mL). After evaporation of toluene, the mixture was distilled under reduced pressure to gave 25 g of pure product. $^1$H NMR(CDCl$_3$): δ1.31(s, 3H, —CH$_3$); 1.72(m, 2H, CH$_2$=CHCH$_2$CH$_2$—); 2.13(m, 2H, CH$_2$=CHCH$_2$CH$_2$—); 3.92(m, 4H, —OCH$_2$CH$_2$O—); 4.95(m, 2H, CH$_2$=CH—); 5.80(m, 1H, CH$_2$=CH—).

EXAMPLE 16

Synthesis of Methyl 2,2-Dimethyl-4-pentenoate 2,2-Dimethyl-4-pentenoic acid (15 g, 0.117 mol) was mixed with 70 mL anhydrous methanol and 50 mL toluene. Concentrated sulfuric acid (0.1 mL) was added. The solution was refluxed for 24 h. Solvents were then removed. The crude product was distilled under reduced pressure to gave 6 g pure product. $^1$H NMR(CDCl$_3$) δ1.28(s, 6H, —CMe$_2$—); 2.37(d, 2H, CH$_2$=CHCH$_2$—); 3.77(s, 3H, —CO$_2$Me); 5.15(m, 2H, CH$_2$=CH—); 5.84(m, 1H, CH$_2$=CH—)

EXAMPLE 17

Synthesis of the Ethylene Copolymer of Methyl 2,2-Dimethyl-4-pentenoate

The compound PdCH$_2$CH$_2$CH$_2$C(O)OCH$_3$[(2,6-i-Pr Ph)$_2$DABMe$_2$]SbF$_6$ (0.0848 9, 0.1 mmol) and methyl 2,2-dimethyl-4-pentenoate (5.545 g, 0.039 mole) were dissolved in 40 mL CH$_2$Cl$_2$. The solution was placed under 1 atm of ethylene under stirring for 60 h at RT. Evaporation of solvent and vacuum drying overnight gave 22.87 g crude product. The copolymer was purified by dissolving the crude product in CH$_2$Cl$_2$ followed by precipitation with methanol. Based on $^1$H NMR(CDCl$_3$), the ester incorporation was 3.5 mole % {δ3.65(s, 3H, —OCH$_3$), the methyl and the other methylene peaks overlapped with the methylene peaks of the copolymers (1.1–1.4)}. The polymer was highly branched based on $^1$H NMR(95Me/1000CH$_2$). The copolymer exhibits a Tg of –65° C. by DSC. GPC (THF, polystyrene standard): Mw=136,000; Mn=78,500; Mw/Mn=1.7.

EXAMPLE 18

Synthesis of the Ethylene Copolymer of Allylpentafluorobenzene)

The compound PdCH$_2$CH$_2$CH$_2$C(O)OCH$_3$[(2,6-i-Pr Ph)$_2$DABMe$_2$]SbF$_6$ (0.0848 g, 0.1 mmol) and allylpentafluorobenzene (5.0 g, 0.024 mole) were dissolved in 40 mL CH$_2$Cl$_2$. The solution was placed under 1 atm of ethylene under stirring for 48 h at RT. Evaporation of solvent and vacuum drying overnight gave 19.45 9 copolymer product. Based on $^1$H NMR(CDCl$_3$), the allylpentafluorobenzene incorporation was 2.0 mole % {δ2.67 (t, 2H, —CH$_2$C$_6$F$_5$)}. The polymer was highly branched based on $^1$H NMR (108Me/1000CH$_2$). $^{19}$F NMR(CD$_2$Cl$_2$, in ppm): –164.4 (s, 2F, m-F), –159.8 (s, 1F, p-F), –145.0 (s, 1.7F, o-F for C$_6$F$_5$—(CH$_2$)$_n$— CHRRÔ, n≧2, R, RÔ=alkyl chain), –143.8 (s, 0.3F, o-F for C$_6$F$_5$—(CH$_2$)$_n$—CHRRÔ, n=1). $^{13}$C NMR also indicated that the percentage of n=1 is about 15%. The copolymer exhibited a Tg of –64° C. by DSC. GPC (THF, polystyrene standard): Mw=120,000; Mn=71,000; Mw/Mn=1.7.

EXAMPLE 19

Synthesis of the Ethylene Copolymer of Allylpentafluorobenzene

The compound [(2,6-i-PrPh)$_2$DABAn]NiBr$_2$ (12 mg, 0.017 mmol) and allylpentafluorobenzene (4.0 g, 0.019 mol) were dissolved in 35 mL toluene in a Schlenk flask in a drybox. This was placed under 1 atm of ethylene in an ice-water bath for 15 min. Two mL PMAO (7.1 wt % toluene solution) was added to the mixture. After stirring under 1 atm of ethylene at 0° C. for 15 min, methanol (100 mL) was slowly added to the reaction mixture followed by 1.5 mL conc. HCl. The white solid polymer was filtered, washed with methanol and dried in vacuo. Copolymer (2.76 g) was obtained. $^1$H NMR (TCE-d$_2$) indicated an allylpentafluorobenzene incorporation of 0.7 mole % [based on the —CH$_2$C$_6$F$_5$ peak (2.73 ppm, t) vs. the methylene, methine (1.1–1.4 ppm) and the methyl peaks (0.8–1.0 ppm) of the copolymer. The polymer was highly branched (104Me/1000CH$_2$). $^{19}$F NMR (TCE-d$_2$, in ppm): –164.0 (s, 2F, m-F), –159.3 (t, 1F, p-F), –144.9 (s, 1.6F, o-F for C$_6$F$_5$—(CH$_2$)$_n$—CHRRÔ, n≧2, R, RÔ=alkyl chain), –143.4 (s, 0.4F, o-F for C$_6$F$_5$—(CH$_2$)$_n$—CHRRÔ, n=1). The copolymer. exhibited a Tg of –52° C. by DSC. GPC (THF, polystyrene standard): Mw=151,000; Mn=91,900; Mw/Mn=1.6.

EXAMPLE 20

Synthesis of 3,3-Dimethyl-1,5-hexadiene

In a dry box, 4.82 g NaH (0.20 mol) was suspended in 100 mL ether in a 500 mL round bottom flask. Methyltriphenylphosphonium bromide, Ph$_3$PCH$_3$Br, (71.9 g, 0.20 mol) was added incrementally. When addition was finished, the slurry became very thick. More ether was added. Soon the reaction mixture became yellow. After stirring at RT for 2 h, the slurry was heated to 50° C. for 1 h. Upon cooling to room temperature, 15 g 2,2-dimethyl-4-pentenal was added. The mixture was stirred at RT. The solution was filtered (product was volatile under vacuum). The solid residue was washed with ether. The filtrate was distilled. The first fraction was ether, the second fraction (4.0 g) was the desired pure product. $^1$HNMR (CDCl$_3$): δ1.00(s, 6H, —CMe$_2$—); 2.05 (d, 2H, CH$_2$=CH—CH$_2$—); 4.98(m, 4H, CH$_2$=CH—CH$_2$— and CH$_2$=CH—CMe$_2$—); 5.80(m, 2H, CH$_2$=CH—CH$_2$— and CH$_2$=CH—CMe$_2$—).

EXAMPLE 21

Synthesis of the Ethylene Copolymer of 3,3-Dimethyl-1,5-hexadiene

The compound PdCH$_2$CH$_2$CH$_2$C(O)OCH$_3$[(2,6-i-Pr Ph)$_2$DABMe$_2$]SbF$_6$ (0.0848 g, 0.1 mmol) and 3,3-dimethyl-1,5-hexadiene (3.384 g, 0.031 mol) were dissolved in 40 mL CH$_2$Cl$_2$. The solution was placed under 1 atm of ethylene under stirring for 60 h at RT. Evaporation of solvent and vacuum drying of the residue overnight gave 1.14 g copolymer product. The $^1$H and $^{13}$C NMR spectra were quite complex and they indicated that 3,3-dimethyl-1,5-hexadiene did incorporate and its insertion could occur on either side of the diene monomer. GPC (THF, polystyrene standard): Mw=5,830; Mn=4,050; Mw/Mn=1.4. The copolymer exhibited a TG of –59° C. by DSC.

EXAMPLE 22

Synthesis of 2-Methyl-4-thia-1,6-heptadiene

To a 250 mL RB flask was added 30 g (0.405 mol) allylmercaptan and 100 mL DMF. Upon cooling in an ice-bath, 9.27 g (0.405 mol) NaH was added in portions under stirring. The mixture was allowed to stir for one hour after completion of the addition. 3-Bromo-2-methylpropene (54.66 g, 0.405 mol) was then added dropwise through an addition funnel. The mixture was allowed to stir for another h after addition was finished. Water and ether were added to the mixture. The ether layer was isolated, washed with water and dried over sodium sulfate. After evaporation of solvent at reduced pressure, the mixture was distilled under full vacuum to give 27.12 g (52%, collected at 34° C./full vacuum) desired product. $^1$H NMR (CDCl$_3$): δ1.92(s, 3H, —CH$_3$) ; 3.15(d, 2H, CH$_2$=CH—CH$_2$—S—) ; 3.17(s, 2H, CH$_2$=C(Me)—CH$_2$—S—); 4.92, 4.97(s, 1H each, CHHÕ=C(Me)—S—, CHHÕ=C(Me)—S—); 5.20(m, 2H, CH$_2$=CH—CH$_2$—S—); 5.88(m, 1H, CH$_2$=CH—CH$_2$—S—).

EXAMPLE 23

Synthesis of Allyl 2-Methyl allyl Sulfone

Oxone(260.3 g, 0.423 mol) was mixed with a slurry of 116.6 g montmorillonite in 200 mL water. Methylene chloride (500 mL) was then added. 2-Methyl-4-thia-1,6-heptadiene (27.1 g, 0.211 mol) was then slowly added to the mixture under stirring. The reaction was exothermic. After stirring for 2 h, the mixture was filtered. The residue was washed with methylene chloride. The organic layer was separated. The water layer was washed with methylene chloride. The combined methylene chloride solution was washed with water and dried over sodium sulfate. Evaporation of solvent under reduced pressure and vacuum distillation of the residue gave 2.5 g desired product(50° C./full vacuum). $^1$H NMR (CDCl$_3$): δ1.95(s, 3H, —CH$_3$) ; 3.64(s, 2H, CH$_2$=C(Me)—CH$_2$—SO$_2$—) ; 3.72(d, 2H, CH$_2$=CH—CH$_2$—SO$_2$—) ; 5.07, 5.22(s, 1H each, CHHÕ=C(Me)—SO$_2$—, CHHÕ=C(Me)—SO$_2$—); 5.46(m, 2H, CH$_2$=CH—CH$_2$—SO$_2$—) ; 5.91(m, 1H, CH$_2$=CH—CH$_2$—SO$_2$—).

EXAMPLE 24

Synthesis of the Ethylene Copolymer of Allyl 2-Methylallyl Sulfone

The compound PdCH$_2$CH$_2$CH$_2$C(O)OCH$_3$[(2,6-i-Pr Ph)$_2$DABMe$_2$]SbF$_6$ (0.0848 g, 0.1 mmol) and allyl 2-methylallyl sulfone (2.4 g, 0.015 mol) were dissolved in 40 mL CH$_2$Cl$_2$. The solution was placed under 1 atm of ethylene under stirring for 37 h at RT. The solution was concentrated to ca. 10 mL and 60 mL of methanol was added. The viscous oil was isolated, redissolved in 10 mL methylene chloride, followed by addition of 60 mL methanol. The viscous oil was isolated and dried in vacuo. Copolymer (0.69 g) was obtained. $^1$H NMR (CD$_2$Cl$_2$) indicated that the allyl 2-methylallyl sulfone incorporation was 0.7 mole %: δ0.8–1.0 (m, —CH$_3$ connected to saturated carbon atoms); 1.0–1.5(m, —CH$_2$—and —CH(R)— connected to saturated carbon atoms); 1.87(m, 2H, —CH$_2$CH$_2$SO$_2$—), 2.04(s, 3H, —SO$_2$CH$_2$(Me)CH=CH$_2$), 3.03(t, 2H, J=4 Hz, —CH$_2$CH$_2$SO$_2$—); 3.72(s, 2H, —SO$_2$CH$_2$(Me)CH=CH$_2$); 5.14, 5.27(s, 1H each, —SO$_2$CH$_2$(Me)CH=CHHÕ and —SO$_2$CH$_2$(Me)CH=CHHÕ). GPC (THF, polystyrene standard): Mw=24,700; Mn=17,200; Mw/Mn=1.4. The copolymer exhibited a Tg of –65° C. by DSC.

EXAMPLE 25

Synthesis of the Ethylene Copolymer of 2,2-Dimethylpent-4-enoic Acid

The compound PdCH$_2$CH$_2$CH$_2$C(O)OCH$_3$[(2,6-i-Pr Ph)$_2$DABMe$_2$]SbF$_6$ (0.0848 g, 0.1 mmol) and 2,2-dimethylpentenoic acid (1.5 g, 0.012 mol) were dissolved in 40 mL CH$_2$Cl$_2$. The solution was placed under 1 atm of ethylene under stirring for 36 h at RT. The reaction was exothermic. The solution was filtered through Celite® and 200 mL methanol was added. The reverse precipitation was repeated once. The viscous oil was isolated and dried in vacuo. Copolymer (12.6 g) was obtained. GPC (THF, polystyrene standard): Mw=59,100; Mn=39,800; Mw/Mn=1.5. The copolymer exhibited a Tg of –69° C. by DSC.

EXAMPLE 26

Synthesis of the Ethylene Copolymer of 2,2-Dimethylpent-4-enoic Acid

The compound PdCH$_2$CH$_2$CH$_2$C(O)OCH$_3$[(2,6-i-Pr Ph)$_2$DABMe$_2$]SbF$_6$ (0.0848 g, 0.1 mmol) and 2,2-dimethylpentenoic acid (5.0 g, 0.039 mol) were dissolved in 40 mL CH$_2$Cl$_2$. The solution was allowed to stir under 1 atm of ethylene at RT for 60 h. Solvent was then evaporated. The viscous residue was heated at 70° C. under full vacuum for 6 h. The residue was then mixed with 100 mL methylene chloride. This mixture was stirred for 30 min. The polymer layer (top) was isolated. Methylene chloride extraction of the acid comonomer was repeated three more times. The viscous oil was isolated and dried in vacuo. Copolymer (11.5 g) was obtained. $^1$H NMR (CD$_2$Cl$_2$) indicated that the incorporation of 2,2-dimethylpentenoic acid was 7.2 mole %: δ0.8–1.0 (m, —CH$_3$ other than —CMe$_2$—); 1.05 (s, 6H, —CMe$_2$—); 1.1–1.5(m, —CH$_2$— and —CH(R)—); 10.38 (s, 1H, —COOH). GPC (THF, polystyrene standard): Mw=53,800; Mn=39,200; Mw/Mn=1.4. The copolymer exhibited a Tg of –59° C. by DSC.

COMPARATIVE EXAMPLE 1

Synthesis of the Ethylene Copolymer of 4-Pentenoic Acid

The compound PdCH$_2$CH$_2$CH$_2$C(O)OCH$_3$[(2,6-i-Pr Ph)$_2$DABMe$_2$]SbF$_6$ (0.0848 g, 0.1 mmol) and 4-pentenoic acid (3.79 g, 0.038 mol) were dissolved in 40 mL CH$_2$Cl$_2$. The solution was allowed to stir under 1 atm of ethylene at room temperature for 64 h. The solution was filtered and subsequently concentrated to ca. 4 mL and was then added 200 mL methanol. The oil at the bottom of the flask was isolated, washed with methanol twice and dried in vacuo. A viscous oily product (0.20 g) was obtained. $^1$H NMR (CD$_2$Cl$_2$) indicated that the incorporation of 4-pentenoic acid was 2.5 mole %: δ0.8–1.0 (m, —CH$_3$Os on the polymer); 1.1–1.5(m, —CH$_2$— and —CH(R)—); 1.60(m, 2H, —CH$_2$CH$_2$CO$_2$H); 2.31(m, 2H, —CH$_2$CH$_2$CO$_2$H); 11.26(s, 1H, —CH$_2$CH$_2$CO$_2$H). The polymer was highly branched: 133Me/1000CH$_2$. GPC (THF, polystyrene standard): Mw=3,430; Mn=2,710; Mw/Mn=1.3. The copolymer exhibited a Tg –58° C. by DSC.

EXAMPLE 27

Synthesis of the Ethylene Copolymer of Allyl Phenyl Sulfone

The compound PdCH$_2$CH$_2$CH$_2$C(O)OCH$_3$[(2,6-i-Pr Ph)$_2$DABMe$_2$]SbF$_6$ (0.0848 g, 0.1 mmol) and allyl phenyl sulfone (5.0 g, 0.027 mol) were dissolved in 40 mL CH$_2$Cl$_2$. The solution was allowed to stir under 1 atm of ethylene at RT for 46 h. The reaction was slightly exothermic. The solution was then concentrated to about 20 mL and 200 mL methanol was added under stirring. The viscous residue was isolated and was dissolved in 25 mL methylene chloride. To this solution was added 150 mL methanol. The polymer was isolated, redissolved in 120 mL methylene chloride and was filtered through Celite®. Solvent was then evaporated under reduced pressure. The viscous oil was dried in vacuo. Copolymer (11.45 g) was obtained. $^1$H NMR (CD$_2$Cl$_2$) indicated that the incorporation of allyl phenyl sulfone was 4.8 mole %: δ0.8–1.0 (m, —CH$_3$Os on the polymer); 1.1–1.5(m, —CH$_2$— and —CH(R)—); 1.75(p, 2H, —CH$_2$CH$_2$SO$_2$Ph) ; 3.20(t, 2H, —CH$_2$SO$_2$Ph); 7.70, 7.78, 7.98(5H total, —SO$_2$C$_6$H$_5$). GPC (THF, polystyrene standard): Mw=112,000; Mn=61,100; Mw/Mn=1.8. The copolymer exhibited a Tg –51° C. by DSC.

EXAMPLE 28

Synthesis of the Ethylene Copolymer of 5-Hexen-2-one

The compound PdCH$_2$CH$_2$CH$_2$C(O)OCH$_3$[(2,6-i-Pr Ph)$_2$DABMe$_2$]SbF$_6$ (0.0848 g, 0.1 mmol) and 5-hexen-2-one (4.24 g, 0.043 mol) were dissolved in 40 mL CH$_2$Cl$_2$. The solution was allowed to stir under 1 atm of ethylene at room temperature for 72 h. The solution was then concentrated to ca. 10 mL and was added methanol. The oil was isolated, washed with 3×5 mL methanol and dried in vacuo. Copolymer (0.31 g) was obtained. $^1$H NMR (CD$_2$Cl$_2$) indicated that the incorporation of 5-hexen-2-one was 4.3 mole %: δ0.88–1.05 (m, —CH$_3$Os on the polymer); 1.10–1.50(m, —CH$_2$— and —CH(R)—); 1.63(m, 2H, —CH$_2$CH$_2$C(O) CH$_3$); 2.19(s, 3H, —C(O)CH$_3$); 2.48(t, 2H, J=7.6 Hz, —CH$_2$CH$_2$C(O)CH$_3$). GPC (THF, polystyrene standard): Mw=6,600; Mn=4,600; Mw/Mn=1.4. The copolymer exhibited a Tg of –70° C. by DSC.

EXAMPLE 29

Synthesis of the Ethylene Copolymer of Diethyl Allylmalonate

The compound PdCH$_2$CH$_2$CH$_2$C(O)OCH$_3$[(2,6-i-Pr Ph)$_2$DABMe$_2$]SbF$_6$ (0.0848 g, 0.1 mmol) and diethyl allylmalonate (5.0 g, 0.025 mol) were dissolved in 40. mL CH$_2$Cl$_2$. The solution was allowed to stir under 1 atm of ethylene at RT for 5 days. Solvent was evaporated and the oily product was dried in vacuo overnight. Copolymer (24.5 g) was obtained. $^1$H NMR (CD$_2$Cl$_2$) indicated that the incorporation of diethyl allylmalonate was 1.7 mole %: δ0.85–1.05 (m, —CH$_3$Os on the polymer); 1.10–1.50(m, —CH$_2$— and —CH(R)— and —CO$_2$CH$_2$CH$_3$); 1.94(m, 2H, —CH$_2$CH(CO$_2$CH$_2$CH$_3$)$_2$); 3.39(t, 1H, —CH$_2$CH (CO$_2$Et)$_2$); 4.25(q, 4H, —CH(CO$_2$CH$_2$CH$_3$)$_2$). The polymer was highly branched: 87Me/1000CH$_2$. GPC (THF, polystyrene standard): Mw=129,000; Mn=82,300; Mw/Mn=1.6. The copolymer exhibited a Tg of –44° C. by DSC.

EXAMPLE 30

Synthesis of the Ethylene Copolymer of Allyl Methyl Carbonate

The compound PdCH$_2$CH$_2$CH$_2$C(O)OCH$_3$[(2,6-i-Pr Ph)$_2$DABMe$_2$]SbF$_6$ (0.0848 9, 0.1 mmol) and allyl methyl carbonate (3.0 g, 0.026 mol) were dissolved in 40 mL CH$_2$Cl$_2$. The solution was allowed to stir under 1 atm of ethylene at room temperature for 66 h. The solution was filtered. Solvent was evaporated. To the residue was added 100 mL methanol. The upper layer was decanted. The oil was dissolved in 4 mL CH$_2$Cl$_2$, followed by addition of 120 mL methanol. The viscous oil was isolated, washed with 2×5 mL methanol and dried in vacuo. Product (0.64 g) was obtained. $^1$H NMR (CD$_2$Cl$_2$) indicated that the incorporation of allyl methyl carbonate was 1.8 mole %: δ0.8–1.0 (m, —CH$_3$Os on the polymer); 1.0–1.4(m, —CH$_2$— and —CH (R)—); 1.62(m, 2H, —CH$_2$CH$_2$OC(O)OCH$_3$); 3.73(s, 3H, —OC(O)OCH$_3$); 4.06(t, J=6.6 Hz, 2H, —CH$_2$CH$_2$OC(O) OCH$_3$). The polymer was highly branched: 108Me/1000CH$_2$. GPC (THF, polystyrene standard): Mw=15,500; Mn=11,700; Mw/Mn=1.3. The copolymer exhibited a Tg of –60° C. by DSC.

EXAMPLE 31

Hydrolysis of the Ethylene Copolymer of Allyl Methyl Carbonate

A mixture of the ethylene copolymer of allyl methyl carbonate of Example 30 (0.38 g,), KOH (0.7 g), diglyme (25 mL) and ethylene glycol (20 mL) was heated at 167° C. for 14 h. Volatiles were evaporated at 80° C. under full vacuum. Residue was washed with 3×5 mL water and then 3×5 mL methanol. The polymer was extracted with 20 mL methylene chloride, filtered and dried in vacuo. Product (50 mg) was obtained. $^1$H NMR (CD$_2$Cl$_2$) indicates that all the carbonate groups were converted to the alcohol groups: δ0.8–1.0 (m, —CH$_3$Os on the polymer); 1.0–1.4(m, —CH$_2$— and —CH(R)—); 1.52(m, 2H, —CH$_2$CH$_2$OH); 3.57(t, J=6.6 Hz, 2H, —CH$_2$OH)

EXAMPLE 32

Synthesis of the Ethylene Copolymer-of 2-Methyl-2-(3-butenyl)-1,3-dioxolane

The compound PdCH$_2$CH$_2$CH$_2$C(O)OCH$_3$[(2,6-i-Pr Ph)$_2$DABMe$_2$]SbF$_6$ (0.0848 g, 0.1 mmol) and 2-methyl-2-(3-butenyl)-1,3-dioxolane (5.0 g, 0.035 mol) were dissolved in 40 mL CH$_2$Cl$_2$. The solution was allowed to stir under 1 atm of ethylene at room temperature for 47 h. The solution was concentrated to ca. 15 mL and then 150 mL methanol was added under stirring. The upper layer was decanted. The oil was redissolved in 20 mL CH$_2$Cl$_2$, followed by addition of 150 mL methanol. The viscous oil was isolated and dried in vacuo. Product (11.9 g) was obtained. $^1$H NMR (CD$_2$Cl$_2$) indicated that the incorporation of 2-methyl-2-(3-butenyl)-1,3-dioxolane was 6.9 mole %: δ0.8–1.0 (m, —CH$_3$Õs on the polymer); 1.0–1.4(m, —CH$_2$— and —CH(R)—, CH$_3$—C(—OR)$_2$CH$_2$—); 1.55(m, 2H, —CH$_2$C(OR)$_2$CH$_3$); 3.85(d, J=3.0 Hz, 4H, —OCHHÕCHHÕ). The polymer was highly branched: 96Me/1000CH$_2$. GPC (THF, polystyrene standard): Mw=63,600; Mn=41,000; Mw/Mn=1.6. The copolymer exhibited a Tg of –65° C. by DSC.

EXAMPLE 33

Synthesis of the Ethylene Copolymer of 4-Allyl-2,3,5,6-tetrafluorobenzoic Acid The compound PdCH$_2$CH$_2$CH$_2$C(O)OCH$_3$[(2,6-i-Pr Ph)$_2$DABMe$_2$]SbF$_6$ (0.0848 g, 0.1 mmol) and 4-allyl-2,3,5,6-tetrafluorobenzoic acid (5.0 g, 0.021 mol) were dissolved in 40 mL CH$_2$Cl$_2$. The solution was allowed to stir under 1 atm of ethylene at RT for 65 h. The solution was concentrated to ca. 40 mL and then 150 mL methanol was added under stirring. The upper layer was decanted. The oil was redissolved in 50 mL CH$_2$Cl$_2$, followed by addition of 150 mL methanol. The reverse precipitation was repeated one more time. The viscous oil was isolated and dried in vacuo, and 7.0 g product was obtained. $^1$H NMR (CD$_2$Cl$_2$) indicated that the incorporation of 4-allyl-2,3,5,6-tetrafluorobenzoic acid was 1.3 mole %: δ0.8–1.0 (m, —CH$_3$Õs on the polymer); 1.0–1.4(m, —CH$_2$— and —CH(R)—); 1.58(m, 2H, —CH$_2$CH$_2$C$_6$F$_4$COOH); 2.73(t, 2H, —CH$_2$CH$_2$C$_6$F$_4$COOH). GPC (THF, polystyrene standard): Mw=13,500; Mn=9,350; Mw/Mn=1.4. The copolymer exhibited a Tg of –65° C. by DSC.

EXAMPLE 34

Synthesis of the Ethylene Copolymer of Allyl 1,1,2,2-Tetrafluoroethyl Ether

The compound PdCH$_2$CH$_2$CH$_2$C(O) OCH$_3$[(2,6-i-Pr Ph)$_2$DABMe$_2$]SbF$_6$ (0.0848 g, 0.1 mmol) and allyl 1,1,2,2-tetrafluoroethyl ether(4.0 g, 0.025 mol) were dissolved in 40 mL CH$_2$Cl$_2$. The solution was allowed to stir under 1 atm of ethylene at room temperature for 37 h. The solution was then concentrated to ca. 10 mL and then 60 mL methanol was added under stirring. The upper layer was decanted. The oil was redissolved in 10 mL CH$_2$Cl$_2$, followed by addition of 60 mL methanol. The viscous oil was isolated and dried in vacuo and 3.55 g product was obtained. $^1$H NMR (CD$_2$Cl$_2$) indicated that the incorporation of allyl 1,1,2,2-tetrafluoroethyl ether was 2.5 mole %: δ0.8–1.0 (m, —CH$_3$ Õs on the polymer); 1.0–1.5(m, —CH$_2$— and —CH(R)—); 1.75(p, 2H, —CH$_2$CH$_2$OCF$_2$CF$_2$H); 4.04(t, 2H, J=6.6 Hz, —CH$_2$CH$_2$OCF$_2$CF$_2$H); 5.78(t, 1H, $^2$J$_{HF}$=52.3 Hz, —CF$_2$H). $^{19}$FNMR (CDCl$_3$): δ–137.0(d, 2F, $^2$J$_{HF}$=53.3 Hz, —CF$_2$CF$_2$H) –91.8(s, 2F, —CF$_2$CF$_2$H). GPC (THF, polystyrene standard): Mw=89,400; Mn=51,300; Mw/Mn=1.7. The copolymer exhibited a Tg of –73° C. by DSC.

EXAMPLE 35

Synthesis of the Ethylene Copolymer of 2,3,4,5,6-Pentafluorostyrene

The compound [(2,6-i-PrPh)$_2$DABAn]NiBr$_2$ (12.2 mg, 0.017 mmol) and 2,3,4,5,6-pentafluorostyrene(4.86 g, 0.025 mol) were dissolved in 35 mL toluene in a Schlenk flask in a drybox. This was placed under 1 atm of ethylene for 15 min. PMAO (2.2 mL, 7.1 wt % toluene solution) was added to the mixture. Reaction was immediately initiated and it was exothermic. Upon stirring at 1 atm of ethylene at RT for 20 min. the flask was chilled with water. Methanol (120 mL) was slowly added to the reaction mixture followed by 1.5 mL conc. HCl. The white solid polymer was filtered, washed with methanol and dried in vacuo, and 2.18 g copolymer was obtained. $^{13}$C NMR indicated that the comonomer incorporation was 1.7 mole %. The copolymer exhibited a Tg of –68° C. by DSC. GPC (TCB, 135° C., PE standard): Mw=79,000; Mn=41,800; Mw/Mn=1.9.

EXAMPLE 36

Synthesis of the Ethylene Copolymer of 2-Allyl-2-methyl-1,3-cyclopentanedione The compound PdCH$_2$CH$_2$CH$_2$C(O)OCH$_3$[(2,6-i-Pr Ph)$_2$DABMe$_2$]SbF$_6$ (0.0848 g, 0.1 mmol) and 2-allyl-2-methyl-1,3-cyclopentanedione (4.18 g, 0.028 mol) were dissolved in 40 mL CH$_2$Cl$_2$. The solution was allowed to stir under 1 atm of ethylene at room temperature for 42 h. The reaction was mildly exothermic. The solution was transferred to a 200 mL RB flask and then 150 mL methanol was added. The upper layer was decanted. The oil was redissolved in 25 mL CH$_2$Cl$_2$, followed by addition of 150 mL methanol. The viscous oil was isolated, washed with 4×10 mL methanol and dried in vacuo, and 9.12 g product was obtained. $^1$H NMR (CD$_2$Cl$_2$) indicated that the incorporation of 2-allyl-2-methyl-1,3-cyclopentanedione was 2.2 mole %: δ0.8–1.0 (m, —CH$_3$Õs on the polymer); 1.13(s, 3H, CH$_3$—C(C(O)CH$_2$—)$_2$CH$_2$—); 1.1-1.5(m, —CH$_2$— and —CH(R)—); 1.63(m, 2H, —CH$_2$C(C(O)CH$_2$—)$_2$CH$_3$); 2.78(s, 4H, —CH$_2$C(C(O)CH$_2$—)$_2$CH$_3$). GPC (THF, polystyrene standard): Mw=60,700; Mn=40,600; Mw/Mn=1.5. The copolymer exhibited a Tg of –62° C. by DSC.

EXAMPLE 37

Synthesis of the Ethylene Copolymer of 2,3,4,5,6-Pentafluorostyrene

The compound PdCH$_2$CH$_2$CH$_2$C(O)OCH$_3$[(2,6-i-Pr Ph)$_2$DABMe$_2$]SbF$_6$ (0.0848 g, 0.1 mmol) and 2,3,4,5,6-pentafluorostyrene (5.0 g, 0.026 mol) were dissolved in 40 mL CH$_2$Cl$_2$. The solution was allowed to stir under 1 atm of ethylene at room temperature for 56 h. The reaction was mildly exothermic. The solution was transferred to a 300 mL RB flask and then 220 mL methanol was added. The upper layer was decanted. The oil was redissolved in 60 mL CH$_2$Cl$_2$, followed by addition of 220 mL methanol. The viscous oil was isolated, washed with 4×15 mL methanol and dried in vacuo, and 24.53 g product was obtained. $^1$H NMR(CD$_2$Cl$_2$) indicated that the incorporation of 2,3,4,5,6-pentafluorostyrene was 0.4 mole %: δ0.8–1.0 (m, —CH$_3$ Õs on the polymer); 1.0–1.5(m, —CH$_2$— and —CH(R)—);

2.68(t, 2H, J=7.3 Hz, —CH$_2$C$_6$F$_5$). $^{19}$FNMR(CD$_2$Cl$_2$): δ–144.8(s, 2F, o-F); –159.3(s, 1F, p-F); –164.0(s, 2F, m-F). Gel permeation chromatography (THF, polystyrene standard): Mw=138,000; Mn=79,100; Mw/Mn=1.7. The copolymer exhibited a Tg of –68° C. by DSC.

EXAMPLE 38

Synthesis of the Ethylene Terpolymer of 7-octenyltrichlorosilane and CH$_2$=CH(CH$_2$)$_4$C$_6$F$_{13}$ The compound PdCH$_2$CH$_2$CH$_2$C(O)OCH$_3$[(2,6-i-Pr Ph)$_2$DABMe$_2$]SbF$_6$ (0.0848 g, 0.1 mmol), 7-octenyltrichlorosilane (1.0 g, 0.0041 mol) and CH$_2$=CH (CH$_2$)$_4$C$_6$F$_{13}$ (6.0 g, 0.015 mol) were dissolved in 40 mL CH$_2$Cl$_2$. The solution was allowed to stir under 1 atm of ethylene at room temperature for 65 h. The solution was concentrated to ca. 20 mL. The flask containing the polymer solution was brought in a drybox under vacuum. Methanol (2 mL) was added to the solution and the mixture was briefly evacuated to give rid of HCl. More methanol (5 mL) was added. The mixture was allowed to stir at RT for 2 h. To the mixture was added 20 mL methanol and this led to the precipitation of the product. This-mixture was allowed to stir for 2 h. Upon addition of 25 mL more methanol, the polymer was isolated as oil. It was redissolved in 8 mL methylene chloride and was precipitated with 40 mL methanol. The viscous oil was isolated and dried in vacuo, and 1.35 g product was obtained. $^1$H NMR(CD$_2$Cl$_2$) indicated that the incorporation of 7-octenyltrichlorosilane was 1.5 mole % and CH$_2$=CH(CH$_2$)$_4$C$_6$F$_{13}$ 7.2 mole %. δ0.70(m, —CH$_2$Si (OMe)$_3$); 0.8-1.0(m, —CH$_3$Os on the polymer); 1.0–1.5(m, —CH$_2$— and —CH(R)—); 1.68(m, —CH$_2$CH$_2$C$_6$F$_{13}$); 2.16 (m, —CH$_2$CH$_2$C$_6$F$_{13}$) 3.62 (s, —CH$_2$Si(OMe)$_3$). GPC (THF, polystyrene standard): Mw=213,000; Mn=54,500; Mw/Mn=3.9. The copolymer exhibited a Tg of –58° C. by DSC.

EXAMPLE 39

Synthesis of the Ethylene Terpolymer of 2,2-Dimethyl-4-pentenoic Acid and CH$_2$=CH(CH$_2$)$_4$C$_6$F$_{13}$ The compound PdCH$_2$CH$_2$CH$_2$C(O)OCH$_3$[(2,6-i-Pr Ph)$_2$DABMe$_2$]SbF$_6$ (0.0848 g, 0.1 mmol), 2,2-dimethyl-4-pentenoic acid (8.65 g, 0.068 mol) and CH$_2$=CH (CH$_2$)$_4$C$_6$F$_{13}$ (8.62 g, 0.021 mole) were dissolved in 30 mL CH$_2$Cl$_2$. The solution was allowed to stir under 1 atm of ethylene at room temperature for 68 h. Solvent was evaporated. The viscous mixture was heated at 85° C. under full vacuum for 22 h to remove unreacted monomers. About 10 g of polymer was obtained. The polymer was partially dehydrated (evidenced by high viscosity) and this made it difficult to quantify the mole percentages of the comonomers from $^1$H NMR. But $^1$H NMR(CD$_2$Cl$_2$) clearly indicated that both 2,2-dimethyl-4-pentenoic acid and CH$_2$=CH (CH$_2$)$_4$C$_6$F$_{13}$ were incorporated in the polymer. δ0.8–1.0(m, —CH$_3$Os on the polymer); 1.0–1.5(m, —CH$_2$— and —CH (R)—, —C(Me)$_2$—); 1.53(m, —CH$_2$CH$_2$C$_6$F$_{13}$); 2.02 (m, —CH$_2$CH$_2$C$_6$F$_{13}$); 10.30 (s, —COOH).

EXAMPLE 40

Preparation of FSO$_2$CF$_2$CON(CH$_3$)CH$_2$CH=CH$_2$

A dried, 3-neck 1-L flask equipped with a Teflon®-coated stir-bar and topped with an addition funnel, septum, and dry ice condenser further attached to a nitrogen source was charged with FSO$_2$CF$_2$COF (52 g, 0.29 mol), diethyl ether (200 mL), and triethylamine (29 mL, 0.21 mol). The mixture was stirred and cooled with an wet ice/water bath, then N-methylallylamine (18 g, 0.25 mol) was added drop-wise via the addition funnel. The mixture was stirred for an additional 3 h and allowed to warm to 25° C. The reaction mixture was poured into 200 mL of ice-cold, dilute HCl, the ether layer was separated, and washed with H$_2$O (8×50 mL), dried (Na$_2$SO$_4$), filtered, and concentrated on a rotary evaporator. Distillation of the residue afforded a 4.51 g forerun and 22.84 g fraction, bp 62–64° C./67 Pa, 98.9–99.6% GC purity, 47% yield. The proton, fluorine, and carbon NMR data confirmed the structure as FSO$_2$CF$_2$CON(CH$_3$) CH$_2$CH=CH$_2$. FTIR (NaCl) 2979.8 cm$^{-1}$ (vw), 1687.2 (vs), 1448.8 (s), 1422.1 (s), 1140.1 (s).

EXAMPLE 41

Ethylene Copolymer of FSO$_2$CF$_2$CON(CH$_3$) CH$_2$CH=CH$_2$

The compound PdCH$_2$CH$_2$CH$_2$C(O)OCH$_3$[(2,6-i-Pr$_2$ Ph)$_2$DAB(Me$_2$)]SbF$_6$ (0.0848 g, 0.1 mmol) and FSO$_2$CF$_2$CON(CH$_3$)CH$_2$CH=CH$_2$ (4.93 g, 0.025 mol) were dissolved in 40 mL CH$_2$Cl$_2$. The solution was placed under 1 atm of ethylene under stirring for 22 h at RT. The reaction was exothermic. The mixture was transferred to a 300 mL RB flask and was added 200 mL methanol under stirring. The oil was isolated and was redissolved in 30 mL CH$_2$Cl$_2$, followed by addition of 200 mL methanol. The oil was isolated, followed by 3×20 mL methanol wash and dried in vacuo. A viscous oil (10.0 g) was obtained. Based on $^{13}$C-NMR, the partially fluorinated monomer incorporation was 2.4 mole %. The polymer was highly branched based on $^{13}$CNMR. The copolymer exhibits a glass transition temperature of –65° C. by DSC. GPC (THF, polyethylene standard): Mw=102,000; Mn=55,500; Mw/Mn=1.8.

EXAMPLE 42

Copolymerization of Ethylene and Ethyl-4-Pentenoate

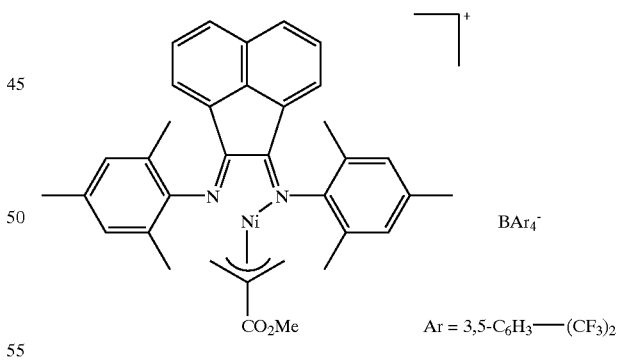

In a drybox, a glass insert was loaded with the nickel complex shown above (0.0311 g, 0.0216 mmol), B(C$_6$F$_5$)$_3$ (0.2076 g, 0.4055 mmol, 18.8 equiv), 3.5 mL of 1,2,4-trichlorobenzene, 1 mL of Et$_2$O, and 0.5 mL of ethyl-4-pentenoate (H$_2$C=CHCH$_2$CH$_2$CO$_2$Et). The insert was then loaded in a pressure tube inside the drybox. The sealed pressure tube was removed from the drybox, attached to an ethylene source, and pressurized with 2.1 MPa of ethylene at RT and then shaken for 18 h. Following precipitation of the reaction mixture in methanol and drying of the isolated product under vacuum, 0.026 g of the copolymer of ethylene and ethyl-4-pentenoate was isolated. H NMR Analysis (TCE, 386° K): 0.8 mol % (3.4 wt %) ethyl-4-pentenoate incorporation in the copolymer; 8.4 total methyl-ended branches per 1000 $CH_2$'s; olefinic end groups were not detectable for Mn determination.

EXAMPLE 43

Copolymerization of Ethylene and Ethyl-4-Pentenoate

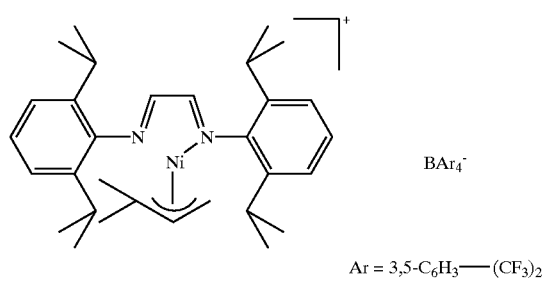

Ar = 3,5-$C_6H_3$—$(CF_3)_2$

In a drybox, a glass insert was loaded with the nickel complex shown above (0.0277 g, 0.0203 mmol), $B(C_6F_5)_3$ (0.2295 g, 0.4483 mmol, 22.1 equiv), 4.5 mL of 1,2,4-trichlorobenzene, and 0.5 mL of ethyl-4-pentenoate ($H_2C=CHCH_2CH_2CO_2Et$). The insert was then loaded in a pressure tube inside the drybox. The sealed pressure tube was removed from the drybox, attached to an ethylene source, and pressurized with 2.1 MPa of ethylene at RT and then shaken for 18 h. Following precipitation of the reaction mixture in methanol and drying of the isolated product under vacuum, 0.138 g of the copolymer of ethylene and ethyl-4-pentenoate was isolated. $^1$H NMR Analysis (TCE, 386° K): 0.4 mol % (1.8 wt %) ethyl-4-pentenoate incorporation in the copolymer; 9.3 total methyl-ended branches per 1000 $CH_2$'s; $M_n$=10,520.

EXAMPLE 44

Copolymerization of Ethylene and the Methyl Ether of ω-Undecylenyl Alcohol

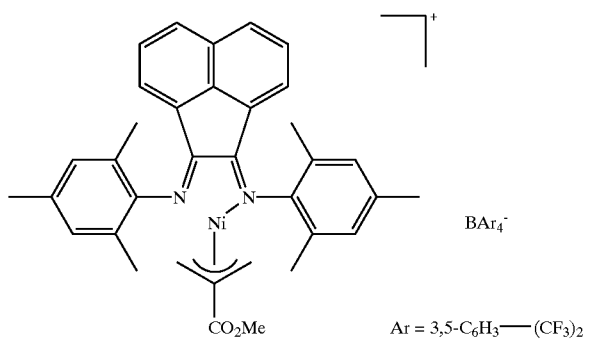

Ar = 3,5-$C_6H_3$—$(CF_3)_2$

In a drybox, a glass insert was loaded with the nickel complex shown above (0.0308 g, 0.0214 mmol), $B(C_6F_5)_3$ (0.2084 g, 0.4071 mmol, 19.0 equiv), 4.5 mL of 1,2,4-trichlorobenzene, and 0.5 mL of the methyl ether of ω-undecylenyl alcohol ($H_2C=CH(CH_2)_9OMe$). The insert was then loaded in a pressure tube inside the drybox. The sealed pressure tube was removed from the drybox, attached to an ethylene source, and pressurized with 2.1 MPa of ethylene at RT and then shaken for 18 h. Following precipitation of the reaction mixture in methanol and drying of the isolated product under vacuum, 2.912 g of the copolymer of ethylene and the methyl ether of ω-undecylenyl alcohol was isolated. $^1$H NMR Analysis (TCE, 386° K): 3.5 mol % (19.4 wt %) incorporation of the methyl ether of ω-undecylenyl alcohol in the copolymer; 26.8 total methyl-ended branches per 1000 $CH_2$'s; $M_n$=28,570.

EXAMPLE 45

Copolymerization of Ethylene and 4-Phenyl-1-Butene

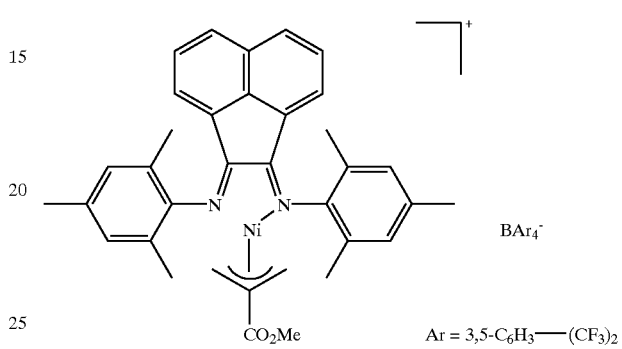

Ar = 3,5-$C_6H_3$—$(CF_3)_2$

In a drybox, a glass insert was loaded with the nickel complex shown above (0.0306 g, 0.0213 mmol), $B(C_6F_5)_3$ (0.2114 g, 0.4130 mmol, 19.4 equiv), 4.5 mL of 1,2,4-trichlorobenzene, and 0.5 mL of 4-phenyl-1-butene ($H_2C=CHCH_2CH_2Ph$). The insert was then loaded in a pressure tube inside the drybox. The sealed pressure tube was removed from the drybox, attached to an ethylene source, and pressurized with 2.1 MPa of ethylene at RT and then shaken for 18 h. Following precipitation of the reaction mixture in methanol and drying of the isolated product under vacuum, 0.81 g of the copolymer of ethylene and 4-phenyl-1-butene was isolated. H NMR Analysis (TCE, 386° K): 0.7 mol % (3.4 wt %) incorporation of 4-phenyl-1-butene in the copolymer; 14.9 total methyl-ended branches per 1000 $CH_2$'s; Mn=46,850.

EXAMPLE 46

Copolymerization of Ethylene and 4-Penten-1-yl Acetate

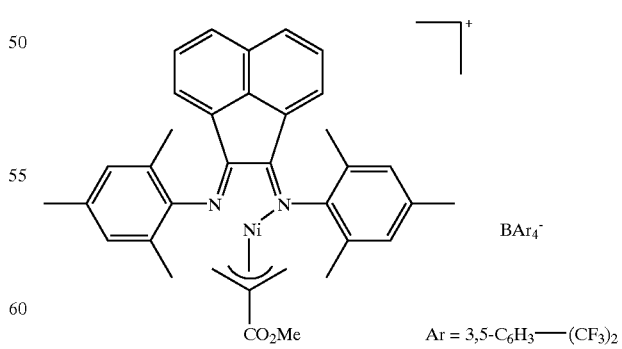

Ar = 3,5-$C_6H_3$—$(CF_3)_2$

In a drybox, a glass insert was loaded with the nickel complex shown above (0.0327 g, 0.0227 mmol), $B(C_6F_5)_3$ (0.2191 g, 0.4280 mmol, 18.9 equiv), 4.5 mL of 1,2,4-trichlorobenzene, and 0.5 mL of 4-penten-1-yl acetate ($H_2C=CH(CH_2)_3OC(O)Me$). The insert was then loaded in a pressure tube inside the drybox. The sealed pressure tube was removed from the drybox, attached to an ethylene source, and pressurized with 2.1 MPa of ethylene at RT and then shaken for 18 h. Following precipitation of the reaction mixture in methanol and drying of the isolated product under vacuum, 1.444 g of the copolymer of ethylene and 4-penten-1-yl acetate was isolated. $^1$H NMR Analysis (TCE, 386° K): 0.7 mol % (3.1 wt %) incorporation of 4-penten-1-yl acetate in the copolymer; 6.0 total methyl-ended branches per 1000 $CH_2$'s; Mn=45,120.

EXAMPLE 47

Copolymerization of Ethylene and Methyl-3,3-Dimethyl-4-Pentenoate

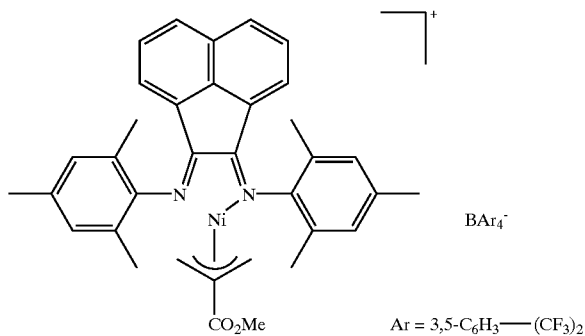

In a drybox, a glass insert was loaded with the nickel complex shown above (0.0297 g, 0.0207 mmol), $B(C_6F_5)_3$ (0.2095 g, 0.4093 mmol, 19.8 equiv) , 4.5 mL of 1,2,4-trichlorobenzene, and 0.5 mL of methyl-3,3-dimethyl-4-pentenoate ($H_2C=CHC(Me)_2CH_2CO_2Me$). The insert was then loaded in a pressure tube inside the drybox. The sealed pressure tube was removed from the drybox, attached to an ethylene source, and pressurized with 2.1 MPa of ethylene at RT and then shaken for 18 h. Following precipitation of the reaction mixture in methanol and drying of the isolated product under vacuum, 1.153 g of the copolymer of ethylene and methyl-3,3-dimethyl-4-pentenoate was isolated. $^1$H NMR Analysis (TCE, 386° K): 0.2 wt % incorporation of methyl-3,3-dimethyl-4-pentenoate in the copolymer; 7.9 total methyl-ended branches per 1000 $CH_2$'s; Mn=39,410.

What is claimed is:

1. A copolymer comprising repeat units of the formula

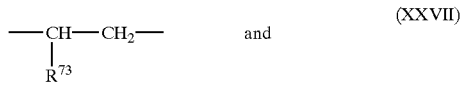

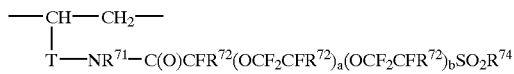

wherein:

T is alkylene or substituted alkylene;

$R^{71}$ is hydrocarbyl or substituted hydrocarbyl;

each $R^{72}$ is independently fluorine, chlorine or perfluoroalkyl containing 1 to 10 carbon atoms;

a is 0, 1 or 2;

b is 0 or an integer of 1 to 6;

$R^{73}$ is alkyl or hydrogen; and $R^{74}$ is hydroxyl, fluorine, chlorine, or OM, wherein M is a metal cation.

2. The copolymer as recited in claim 1 wherein:

$R^{71}$ is alkyl;

each $R^{72}$ is independently fluorine or trifluoromethyl; and $R^{74}$ is fluorine, hydroxyl or OM, wherein M is an alkali metal cation.

3. The copolymer as recited in claim 1 wherein:

T is —$(CH_2)_n$— wherein n is 1;

$R^{71}$ is methyl;

each $R^{72}$ is fluorine;

a is 0;

b is 0; and $R^{74}$ is fluorine, hydroxyl or OM, wherein M is an alkali metal cation.

4. The copolymer of claim 2 wherein $R^{73}$ is hydrogen.

5. The copolymer of claim 1 wherein $R^{73}$ is hydrogen.

6. The copolymer of claim 3 wherein $R^{73}$ is hydrogen.

* * * * *